US010272231B2

(12) United States Patent     (10) Patent No.: US 10,272,231 B2
Kick et al.     (45) Date of Patent: *Apr. 30, 2019

(54) EXPANDABLE TRANS-SEPTAL SHEATH

(71) Applicant: Onset Medical Corporation, Irvine, CA (US)

(72) Inventors: George F. Kick, Casa Grande, AZ (US); Jay A. Lenker, Laguna Beach, CA (US); Edward J. Nance, Corona, CA (US); Joseph Bishop, Menifee, CA (US); Onnik Tchulluian, Carlsbad, CA (US); Huan T. Nguyen, Santa Ana, CA (US)

(73) Assignee: Onset Medical Corporation, Irvine, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 14/052,441

(22) Filed: Oct. 11, 2013

(65) Prior Publication Data

US 2014/0039494 A1     Feb. 6, 2014

Related U.S. Application Data

(63) Continuation of application No. 11/222,498, filed on Sep. 8, 2005, now abandoned.

(Continued)

(51) Int. Cl.
*A61M 29/02*     (2006.01)
*A61B 17/34*     (2006.01)
(Continued)

(52) U.S. Cl.
CPC ......... *A61M 29/02* (2013.01); *A61B 17/3478* (2013.01); *A61B 18/1492* (2013.01);
(Continued)

(58) Field of Classification Search
CPC ............ A61B 17/3423; A61B 17/3431; A61B 17/3439; A61B 2017/3433;
(Continued)

(56) References Cited

U.S. PATENT DOCUMENTS

| 668,879 A | 2/1901 | Miller |
| 1,213,001 A | 1/1917 | Philips |

(Continued)

FOREIGN PATENT DOCUMENTS

| EP | 0 177 177 A2 | 4/1986 |
| EP | 0 249 456 A2 | 12/1987 |

(Continued)

OTHER PUBLICATIONS

International Search Report for Application No. PCT/US05/32291 dated Apr. 3, 2007.

(Continued)

*Primary Examiner* — Katherine M Rodjom
(74) *Attorney, Agent, or Firm* — Inskeep IP Group, Inc.

(57) ABSTRACT

Disclosed is an expandable transluminal sheath, for introduction into the body while in a first, low cross-sectional area configuration, and subsequent expansion of at least a part of the distal end of the sheath to a second, enlarged cross-sectional configuration. The sheath is configured for use in the vascular system. The access route is through the inferior vena cava to the right atrium, where a trans-septal puncture, followed by advancement of the catheter is completed. The distal end of the sheath is maintained in the first, low cross-sectional configuration during advancement through the atrial septum into the left atrium. The distal end of the sheath is expanded using a radial dilator. In one application, the sheath is utilized to provide access for a diagnostic or therapeutic procedure such as electrophysiological mapping of the heart, radio-frequency ablation of (Continued)

left atrial tissue, placement of atrial implants, valve repair, or the like.

12 Claims, 21 Drawing Sheets

Related U.S. Application Data

(60) Provisional application No. 60/709,240, filed on Aug. 18, 2005, provisional application No. 60/674,226, filed on Apr. 22, 2005, provisional application No. 60/660,512, filed on Mar. 9, 2005, provisional application No. 60/608,355, filed on Sep. 9, 2004.

(51) Int. Cl.
    *A61F 2/24*     (2006.01)
    *A61M 25/06*     (2006.01)
    *A61B 18/14*     (2006.01)
    *A61M 25/09*     (2006.01)
    *A61B 17/00*     (2006.01)
    *A61B 18/00*     (2006.01)
    *A61M 25/00*     (2006.01)
    *A61M 25/10*     (2013.01)
    *A61M 25/01*     (2006.01)

(52) U.S. Cl.
    CPC ....... *A61F 2/2427* (2013.01); *A61M 25/0662* (2013.01); *A61M 25/09* (2013.01); *A61B 17/3431* (2013.01); *A61B 17/3439* (2013.01); *A61B 2017/00247* (2013.01); *A61B 2017/00323* (2013.01); *A61B 2018/00392* (2013.01); *A61M 25/0045* (2013.01); *A61M 25/0053* (2013.01); *A61M 25/0084* (2013.01); *A61M 25/0097* (2013.01); *A61M 25/1011* (2013.01); *A61M 2025/0024* (2013.01); *A61M 2025/0175* (2013.01); *A61M 2025/0681* (2013.01)

(58) Field of Classification Search
    CPC .. A61B 2017/3445; A61B 2017/00243; A61B 2017/00292; A61B 2017/3486; A61B 2017/3488; A61M 25/065; A61M 25/0662; A61M 2025/0024; A61M 2025/0025

See application file for complete search history.

(56) References Cited

U.S. PATENT DOCUMENTS

| | | |
|---|---|---|
| 1,248,492 A | 12/1917 | Hill |
| 2,548,602 A | 4/1948 | Greenburg |
| 3,509,883 A | 5/1970 | Dibelius |
| 3,545,443 A | 12/1970 | Ansari |
| 3,742,958 A | 7/1973 | Rundles |
| 3,789,852 A | 2/1974 | Kim et al. |
| 3,874,388 A | 4/1975 | King et al. |
| 3,902,492 A | 9/1975 | Greenhalgh |
| 4,018,230 A | 4/1977 | Ochiai et al. |
| 4,141,364 A | 2/1979 | Schultze |
| 4,338,942 A | 7/1982 | Fogarty |
| 4,401,433 A | 8/1983 | Luther |
| 4,411,655 A | 10/1983 | Schreck |
| 4,451,256 A | 5/1984 | Weikl et al. |
| 4,479,497 A | 10/1984 | Fogarty et al. |
| 4,581,025 A | 4/1986 | Timmermans |
| 4,589,868 A | 5/1986 | Dretler |
| 4,601,713 A | 7/1986 | Fuqua |
| 4,610,668 A | 9/1986 | Silvestrini et al. |
| 4,650,466 A | 3/1987 | Luther |
| 4,710,181 A * | 12/1987 | Fuqua ............... A61M 25/0023 604/103.05 |
| 4,716,901 A | 1/1988 | Jackson et al. |
| 4,738,666 A | 4/1988 | Fuqua |
| 4,739,762 A | 4/1988 | Palmaz |
| 4,772,266 A | 9/1988 | Groshong |
| 4,790,817 A | 12/1988 | Luther |
| 4,798,193 A | 1/1989 | Giesy et al. |
| 4,846,791 A | 7/1989 | Hattler et al. |
| 4,865,593 A | 9/1989 | Ogawa et al. |
| 4,869,717 A | 9/1989 | Adair |
| 4,888,000 A | 12/1989 | McQuilkin et al. |
| 4,896,669 A | 1/1990 | Bhate et al. |
| 4,899,729 A | 2/1990 | Gill et al. |
| 4,921,479 A | 5/1990 | Grayzel |
| 4,954,126 A | 9/1990 | Wallsten |
| 4,955,895 A | 9/1990 | Sugiyama et al. |
| 4,972,827 A | 11/1990 | Kishi et al. |
| 4,986,830 A | 1/1991 | Owens et al. |
| 5,011,488 A | 4/1991 | Ginsburg et al. |
| 5,045,056 A | 9/1991 | Behl |
| 5,059,183 A | 10/1991 | Semrad |
| 5,078,736 A | 1/1992 | Behl |
| 5,092,839 A | 3/1992 | Kipperman |
| 5,100,388 A | 3/1992 | Behl et al. |
| 5,108,413 A | 4/1992 | Moyers |
| 5,112,304 A | 5/1992 | Barlow et al. |
| 5,112,308 A | 5/1992 | Olsen et al. |
| 5,116,318 A | 5/1992 | Hillstead |
| 5,122,122 A | 6/1992 | Allgood |
| 5,139,511 A | 8/1992 | Gill et al. |
| 5,158,545 A | 10/1992 | Trudell et al. |
| 5,176,659 A | 1/1993 | Mancini |
| 5,183,464 A | 2/1993 | Dubrul et al. |
| 5,188,602 A | 2/1993 | Nichols |
| 5,190,528 A | 3/1993 | Fonger et al. |
| 5,201,756 A | 4/1993 | Horzewski et al. |
| 5,222,938 A | 6/1993 | Behl |
| 5,222,971 A | 6/1993 | Willard et al. |
| 5,224,935 A | 7/1993 | Hollands |
| 5,234,425 A | 8/1993 | Fogarty et al. |
| 5,250,025 A | 10/1993 | Sosnowski et al. |
| 5,250,033 A | 10/1993 | Evans et al. |
| 5,275,611 A | 1/1994 | Behl |
| 5,295,994 A | 3/1994 | Bonutti |
| 5,312,360 A | 5/1994 | Behl |
| 5,316,360 A | 5/1994 | Feikma |
| 5,318,588 A | 6/1994 | Horzewski et al. |
| 5,320,611 A | 6/1994 | Bonutti et al. |
| 5,324,261 A | 6/1994 | Amundson et al. |
| 5,346,503 A | 9/1994 | Chow et al. |
| 5,380,304 A | 1/1995 | Parker |
| 5,392,766 A | 2/1995 | Masterson et al. |
| 5,395,341 A | 3/1995 | Slater |
| 5,395,349 A | 3/1995 | Quiachon et al. |
| 5,407,430 A | 4/1995 | Peters |
| 5,409,469 A | 4/1995 | Schaerf |
| 5,431,676 A | 7/1995 | Dubrul et al. |
| 5,433,708 A | 7/1995 | Nichols et al. |
| 5,454,790 A | 10/1995 | Dubrul |
| 5,460,170 A | 10/1995 | Hammerslag |
| 5,514,091 A | 5/1996 | Yoon |
| 5,514,236 A | 5/1996 | Avellanet et al. |
| 5,527,336 A | 6/1996 | Rosenbluth |
| 5,540,658 A | 7/1996 | Evans et al. |
| 5,542,928 A | 8/1996 | Evans et al. |
| 5,662,614 A | 9/1997 | Edoga |
| 5,662,700 A | 9/1997 | Lazarus |
| 5,674,857 A | 10/1997 | Anderson et al. |
| 5,676,693 A | 10/1997 | LaFontaine |
| 5,700,253 A | 12/1997 | Parker |
| 5,713,867 A | 2/1998 | Morris |
| 5,738,667 A | 4/1998 | Solar |
| 5,746,745 A * | 5/1998 | Abele ............... A61F 2/958 604/103.08 |
| 5,766,203 A | 6/1998 | Imran et al. |
| 5,776,141 A | 7/1998 | Klein et al. |
| 5,846,251 A | 12/1998 | Hart |
| 5,885,217 A | 3/1999 | Gisselberg et al. |

(56) References Cited

U.S. PATENT DOCUMENTS

| | | |
|---|---|---|
| 5,888,196 A | 3/1999 | Bonutti |
| 5,916,145 A | 7/1999 | Chu et al. |
| 5,964,730 A | 10/1999 | Williams et al. |
| 5,971,938 A | 10/1999 | Hart et al. |
| 5,997,508 A | 12/1999 | Lunn et al. |
| 6,080,174 A | 6/2000 | Dubrul et al. |
| 6,090,072 A | 7/2000 | Kratoska et al. |
| 6,120,480 A | 9/2000 | Zhang et al. |
| 6,120,494 A | 9/2000 | Jonkman |
| 6,123,689 A | 9/2000 | To et al. |
| 6,168,579 B1 | 1/2001 | Tsugita |
| 6,183,443 B1 | 2/2001 | Kratoska et al. |
| 6,197,016 B1 | 3/2001 | Fourkas et al. |
| 6,228,052 B1 | 5/2001 | Pohndorf |
| 6,293,909 B1 | 9/2001 | Chu et al. |
| 6,312,443 B1 | 11/2001 | Stone |
| 6,346,074 B1 * | 2/2002 | Roth ............... A61B 17/00234 600/121 |
| 6,358,238 B1 | 3/2002 | Sherry |
| 6,447,540 B1 | 9/2002 | Fontaine et al. |
| 6,471,684 B2 | 10/2002 | Dulak et al. |
| 6,494,860 B2 | 12/2002 | Rocamora et al. |
| 6,494,893 B2 | 12/2002 | Dubrul et al. |
| 6,524,268 B2 | 2/2003 | Hayner et al. |
| 6,530,902 B1 | 3/2003 | Jonkman |
| 6,537,247 B2 | 3/2003 | Shannon |
| 6,582,395 B1 | 6/2003 | Burkett et al. |
| 6,613,062 B1 | 9/2003 | Leckrone et al. |
| 6,616,678 B2 | 9/2003 | Nishtala et al. |
| 6,679,902 B1 | 1/2004 | Boyle et al. |
| 6,692,462 B2 | 2/2004 | Mackenzie et al. |
| 6,692,482 B2 | 2/2004 | Heller et al. |
| 7,090,683 B2 * | 8/2006 | Brock ............... A61B 17/0469 606/1 |
| 8,900,214 B2 * | 12/2014 | Nance et al. ............... 604/509 |
| 2001/0012950 A1 | 8/2001 | Nishtala et al. |
| 2001/0037126 A1 | 11/2001 | Stack et al. |
| 2002/0009535 A1 | 1/2002 | Michel et al. |
| 2002/0010476 A1 | 1/2002 | Mulholland et al. |
| 2002/0077653 A1 | 6/2002 | Hudson et al. |
| 2002/0096183 A1 | 7/2002 | Stevens et al. |
| 2002/0099431 A1 | 7/2002 | Armstrong et al. |
| 2002/0169377 A1 * | 11/2002 | Khairkhahan ... A61B 17/32037 600/433 |
| 2003/0050600 A1 | 3/2003 | Ressemann et al. |
| 2003/0135156 A1 | 7/2003 | Bencini et al. |
| 2003/0212384 A1 * | 11/2003 | Hayden ............... A61M 29/02 604/533 |
| 2004/0006344 A1 | 1/2004 | Nguyen et al. |
| 2005/0085842 A1 | 4/2005 | Eversull et al. |
| 2005/0124937 A1 | 6/2005 | Kick et al. |
| 2005/0149105 A1 | 7/2005 | Leeflang et al. |
| 2005/0222576 A1 | 10/2005 | Kick et al. |
| 2005/0228452 A1 * | 10/2005 | Mourlas ............... A61B 1/00071 607/3 |
| 2006/0135962 A1 | 6/2006 | Kick et al. |
| 2007/0239170 A1 | 10/2007 | Brock et al. |

FOREIGN PATENT DOCUMENTS

| | | |
|---|---|---|
| EP | 0 385 920 A2 | 9/1990 |
| EP | 0 206 553 B1 | 1/1991 |
| EP | 0 421 650 A1 | 4/1991 |
| EP | 0 546 766 A2 | 6/1993 |
| JP | 9-501594 | 2/1997 |
| JP | 10-505767 | 6/1998 |
| JP | 2003-530190 | 10/2003 |
| WO | WO 92/19312 A1 | 11/1992 |
| WO | WO 95/05207 | 2/1995 |
| WO | WO 95/30374 A1 | 11/1995 |
| WO | WO 96/08286 | 3/1996 |
| WO | WO 99/16499 A1 | 4/1999 |
| WO | WO 1999/017665 | 4/1999 |
| WO | WO 01/078596 | 10/2001 |
| WO | WO 03/011154 | 2/2003 |
| WO | WO 03/077733 | 9/2003 |
| WO | WO 03/090834 A2 | 11/2003 |

OTHER PUBLICATIONS

Mar. 2, 2011 Office Action for Japanese Application No. 2007-531403.
Mar. 21, 2012 Office Action for Japanese Application No. 2007-531403.
Apr. 25, 2012 Extended Search Report for European Application No. 05796582.4.

* cited by examiner

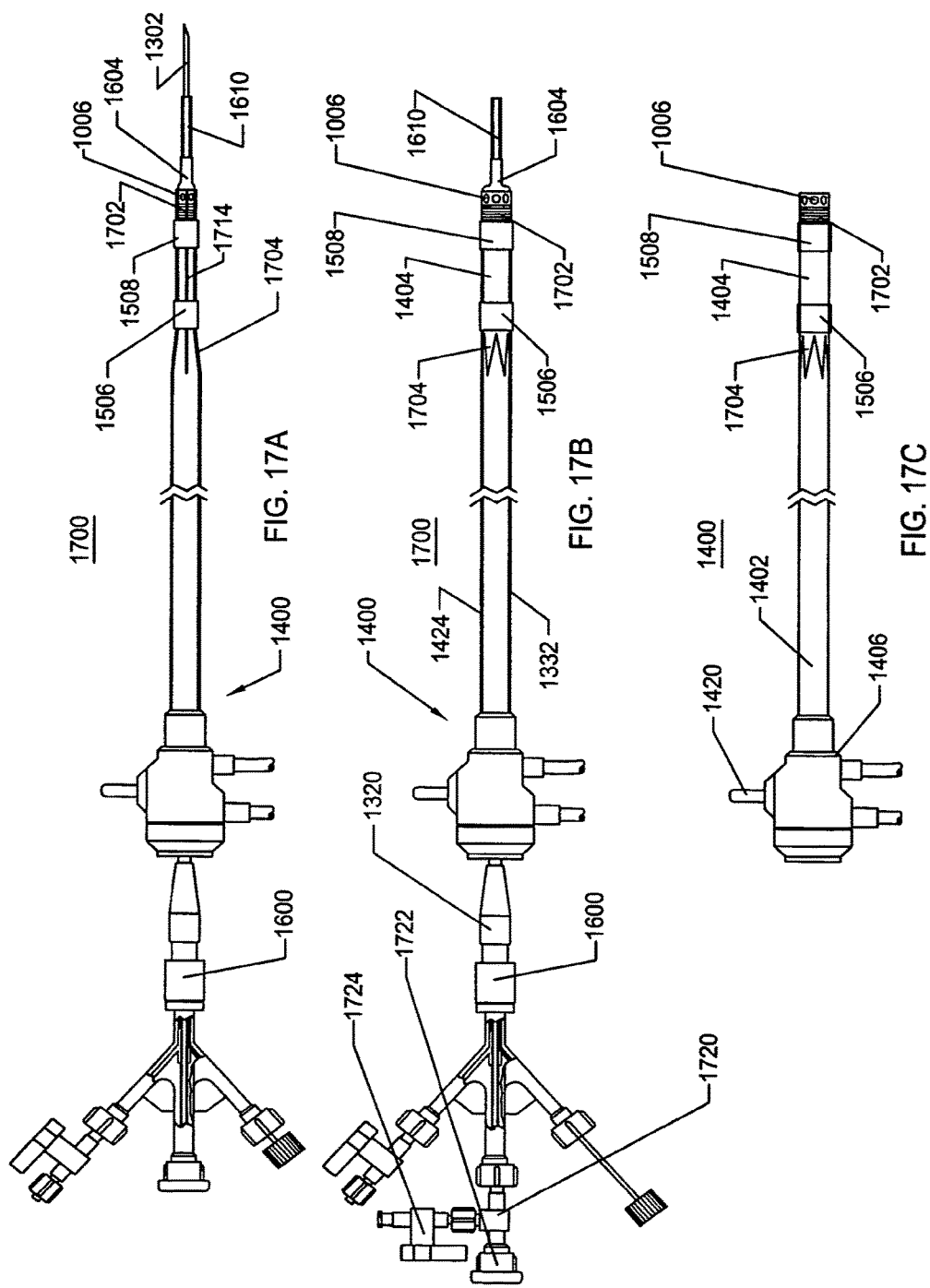

EXPANDABLE TRANS-SEPTAL SHEATH

PRIORITY CLAIM

This application is a continuation of U.S. patent application Ser. No. 11/222,498, filed Sep. 8, 2005, which claims the benefit of priority to U.S. application Ser. No. 60/709,240, filed Aug. 18, 2005, U.S. Application Ser. No. 60/674,226, filed Apr. 22, 2005, U.S. Application Ser. No. 60/660,512, filed on Mar. 9, 2005, and U.S. Provisional Application Ser. No. 60/608,355, filed on Sep. 9, 2004. Each of the foregoing applications is hereby incorporated by reference in its entirety.

BACKGROUND OF THE INVENTION

Field of the Invention

The invention relates to medical devices and, more particularly, to methods and devices for accessing the cardiovascular system.

Description of the Related Art

A wide variety of diagnostic or therapeutic procedures involves the introduction of a device into the vasculature through a percutaneous incision at an access site. Such regions of the vasculature, preferred for access, include both the arteries and veins, typically at peripheral locations in the body. Typical access sites include the jugular vein, the subclavian artery, the subclavian vein, the brachial artery, the femoral arteries and the femoral veins. Techniques commonly known for such vascular access include the Seldinger technique. The Seldinger technique involves using a hollow needle to puncture the skin and gain access to the selected artery or vein. A guidewire is next placed through the hollow needle into the selected region of vasculature. The guidewire may be advanced to a target location in the vasculature, often more than 100 cm away from the access site. The needle is removed and a tapered dilator with a sheath and a central lumen in the dilator is advanced over the guidewire into the vasculature. The dilator is next removed and a guide catheter is advanced through the sheath over the guidewire. The guide catheter can be advanced all the way, or part way, to the target site. The guide catheter, following, or without, removal of the guidewire can be used for directing therapeutic or diagnostic catheters to regions of the vasculature and central circulation, including external and internal structures of the heart. A general objective of access systems, which have been developed for this purpose, is to minimize the cross-sectional area of the access lumen, while maximizing the available space for the diagnostic or therapeutic catheter placement therethrough. These procedures are especially suited for coronary angioplasty, stent placement, cerebrovascular coil placement, diagnostic cardiac catheterization, and the like.

Electrophysiology (EP) mapping and cardiac tissue ablation procedures are examples of diagnostic or therapeutic interventional procedures that are commonly performed on the heart. The procedure involves the steps of inserting a hollow needle, with a hemostasis valve affixed to its proximal end, into the femoral vein via a percutaneous puncture. A guidewire is next inserted through the hemostasis valve and the central lumen of the needle into the femoral vein. The guidewire is routed, under fluoroscopic control, cranially toward the heart until it reaches the right atrium via the inferior vena cava. The hollow needle is removed and a sheath with a tapered tip central obturator further including a central guidewire lumen, termed a dilator, is routed over the guidewire, through the skin puncture, through the wall of the femoral vein, and into the central lumen of the femoral vein. The central obturator or dilator is next removed. A Mullins catheter is next routed through the sheath, over the guidewire, and advanced to the right atrium. The guidewire is removed and a Brockenbrough™ (Trademark of C.R. Bard, Inc.)—type needle is inserted through the proximal end of the Mullins™ catheter and routed to the right atrium. The Mullins catheter is positioned, under fluoroscopic guidance, so that its distal end is located in the Foramenal valley, a feature in the septal wall of myocardium that divides the right atrium from the left atrium. The Foramenal valley is the remains of a communication between the right and left atrium, which exists prior to birth, but which closes following birth due to the pressures imposed by the beating heart of the newborn infant. The Brockenbrough needle is next advanced through the atrial septum in the general region of the Foramenal valley. The Mullins catheter is next advanced over the Brockenbrough needle until its distal end resides within the left atrium. Hemostatic valves at the proximal end of all hollow devices permit sealing around catheters and devices inserted therethrough with corresponding prevention or minimization of blood loss and the entry of air.

The procedure continues with the Brockenbrough needle being withdrawn and replaced with a 0.032 to 0.038 inch diameter guidewire, generally of the stiff variety. This guidewire may have a bifurcated distal end to prevent inadvertent retraction once the guidewire has been advanced and expanded into the left atrium. The Mullins catheter is next withdrawn and replaced with a guide catheter having internal dimensions generally around 8 French and a tapered, removable obturator. The guide catheter is advanced into the right atrium and across the atrial septum, following which the obturator is removed. At this time, diagnostic and therapeutic catheters can be advanced into the left atrium so that appropriate EP mapping and ablation can occur. However, problems sometimes arise, when trying to pass the guide catheter across the atrial septum, in that the tract generated by the Brockenbrough needle and Mullins catheter closes too tightly to allow passage of the guide catheter. At this point, a balloon catheter is advanced over the guidewire and through the guide catheter. The balloon catheter is advanced so that its dilatation balloon traverses the atrial septum. The balloon catheter is next inflated to stretch the tissues surrounding the atrial septal puncture. At this time, the guide catheter can have its dilator re-inserted and the entire assembly advanced over the guidewire through the atrial septum and into the left atrium.

Current therapeutic techniques may involve advancing an EP mapping catheter through the guide catheter and positioning the EP mapping catheter at various locations within the left atrium. Electrocardiogram signals are sensed by the EP mapping catheter. These signals are conducted or transmitted from the distal tip to the proximal end over electrical lines routed along the length of the EP catheter. The signals are analyzed by equipment electrically connected to the proximal end of the EP mapping catheter. Catheter guidance is generally accomplished using X-ray fluoroscopy, ultrasound imaging such as ICE, TEE, and the like. Therapy generally involves radio-frequency (RF) electromagnetic wave generation by external equipment electrically connected to an EP therapeutic catheter. The EP therapeutic catheter is advanced into the left atrium into regions of foci of electrical interference of the hearts normal electrical conduction. Application of such radio-frequency energy at the tip of the EP therapeutic catheter, which is brought into contact with the myocardium, causes tissue ablation and the elimination of the sources of these spurious signals or re-entry waveforms. A primary area targeted for RF tissue ablation is the area surrounding the origin of the pulmonary veins. Often a ring-type electrode is beneficial in performing this procedure. Such tissue ablation can be performed using RF energy to generate heat, but it can also be performed using microwaves, Ohmic heating, high-intensity focused ultrasound (HIFU), or even cryogenic cooling. The cryogenic cooling may have certain advantages relative to heating methodologies in that tissue damage is lessened. Although a single atrial septal puncture may be adequate for electrophysiological mapping of the left atrium, therapeutic systems, including RF ablation devices often require that two atrial septal punctures be performed. A risk of atrial septal punctures includes potentially perforating the aorta, a high-pressure outlet line, which resides quite close to the atrial septum.

Provision is generally made to deflect instrumentation through substantial angles, between 20 and 90 degrees, within the right atrium to gain access to the atrial septum from a catheter routed cranially within the inferior vena cava. To address this situation, the Brockenbrough needle, the Mullins catheter, or both, are substantially curved and significant skill is required, on the part of the cardiologist or electrophysiologist to negotiate the path to the atrial septum and into the left atrium.

One of the primary issues that arise during electrophysiology procedures in the heart is the need to remove and replace multiple instruments multiple times, which is highly expensive and adds substantial time to the conduct of the procedure. A reduction in the number of catheter and guidewire passes and interchanges would reduce procedure time, reduce the risk of complications, improve patient outcomes, reduce procedural cost, and increase the number of cases that could be performed at a given catheterization lab. Current procedures involving multiple atrial septal penetrations would be reduced in frequency or become less time consuming and less risky if only a single atrial septal penetration was necessary. Additional benefit could be derived if larger catheters could be used, thus enabling the use of more sophisticated, powerful, and accurate instruments to improve patient outcomes. The limitations of current systems are accepted by physicians but the need for improved instrumentation is clear. Furthermore, placement of implants within the left atrium, such as the Atritech Watchman™ or the Microvena PLAATO™ would be facilitated if a larger working channel could be made available.

Further reading related to the diagnosis and treatment of atrial fibrillation (AF) includes Hocini, M, et al., Techniques for Curative Treatment of Atrial Fibrillation, J. Cardiovasc Electrophysiol, 15(12): 1467-1471, 2004 and Pappone, C and Santinelli, V, The Who, What, Why, and How-to Guide for Circumferential Pulmonary Vein Ablation, J. Cardiovasc Electrophysiol, 15(10): 1226-1230, 2004. Further reading on RF ablation includes Chandrakantan, A, and Greenberg, M, Radiofrequency Catheter Ablation, eMedicine, topic 2957 Oct. 28, 2004. Further reading regarding catheter approaches to treating pathologies of the left atrium include Ross, et al, Transseptal Left Atrial Puncture; New Technique for the Measurement of Left Atrial Pressure in Man, Am J. Cardiol, 653-655, May 1959 and Changsheng M, et al., Transseptal Approach, an Indispensable Complement to Retrograde Aortic Approach for Radiofrequency Catheter Ablation of Left-Sided Accessory Pathways, J. H K Coll Cardiol, 3: 107-111, 1995.

A need, therefore, remains for improved access technology, which allows a device to be percutaneously or surgically introduced, endovascularly advanced to the right atrium, and enabled to cross the atrial septum by way of a myocardial puncture and Dotter-style follow-through. The device would further permit dilation of the myocardial puncture in the region of the atrial septum so that the sheath could pass relatively large diameter instruments or catheters, or multiple catheters through the same puncture. Such large dilations of the tissues of the atrial septum need to be performed in such a way that the residual defect is minimized when the device is removed. It would be beneficial if a cardiologist or hospital did not need to inventory and use a range of catheter diameters. It would be far more useful if one catheter or sheath diameter could fit the majority of patients or devices. Ideally, the catheter or sheath would be able to enter a vessel or body lumen with a diameter of 3 to 12 French or smaller, and be able to pass instruments through a central lumen that is 14 to 30 French. The sheath or catheter would be capable of gently dilating the atrial septum using radially outwardly directed force and of permitting the exchange of instrumentation therethrough without being removed from the body. The sheath or catheter would also be maximally visible under fluoroscopy and would be relatively inexpensive to manufacture. The sheath or catheter would be kink resistant, provide a stable or stiff platform for atrial septum penetration, and minimize abrasion and damage to instrumentation being passed therethrough. The sheath or catheter would further minimize the potential for injury to body lumen or cavity walls or surrounding structures. The sheath or catheter would further possess certain steering capabilities so that it could be negotiated through substantial curves or tortuosity and permit instrument movement within the sheath.

SUMMARY OF THE INVENTION

Accordingly, an embodiment of the present invention comprises an expandable endovascular access sheath for providing minimally invasive access to a left atrium. An axially elongate sheath tube includes a proximal end, a distal end, and a central through lumen. The sheath has a distal region which is expandable in circumference in response to outward pressure applied therein. A hub is coupled to the proximal end of the sheath tube. The hub is configured to facilitate the passage of instrumentation. An obturator extends through the central lumen and is configured to occlude the central lumen of the sheath during insertion. The obturator comprises an obturator hub that is releasably coupled to the hub of the sheath. A guidewire lumen is within the obturator. The obturator is a balloon dilator capable of expanding the distal region of the sheath from a collapsed configuration to an expanded configuration.

Another embodiment of the present invention is a method of instrumenting a left atrium of a patient. A guidewire is routed into the right atrium from a peripheral vein. A sheath is inserted with a collapsed distal region and a pre-inserted dilator into the patient over the guidewire. The sheath is advanced to a treatment or diagnostic site within the right atrium of the heart. A trans-septal puncture is made between the right and left atrium. The collapsed distal region is advanced through the puncture into the left atrium. The distal region of the sheath is dilated so that the distal region of the sheath is expanded. The dilator is collapsed and removed from the sheath. Instrumentation is inserted through the lumen of the sheath into the left atrium. A therapy or diagnosis procedure is performed with the instrumentation. The sheath is removed from the patient.

Another embodiment of the invention is a sheath adapted for insertion into the right or left atrium of the heart. The sheath has a diametrically collapsed distal end and means for tracking the sheath over an already placed guidewire to a target treatment site in the right or left atrium of the heart. The sheath also includes means for articulating the distal end of the sheath, means for dilating at least a portion of the distal end of the sheath, and means for removal of the sheath from the patient.

In another embodiment, a radially expanding access sheath is used to provide access to the left atrium by way of a trans-septal puncture and advancement in the atrial septum dividing the right and left atriums. In an particular embodiment, the sheath can have an introduction outside diameter that ranges from 3 to 12 French with a preferred range of 5 to 10 French. The diameter of the sheath can be expandable to permit instruments ranging up to 30 French to pass therethrough, with a preferred range of between 3 and 20 French. The sheath can have a working length ranging between 40-cm and 200-cm with a preferred length of 75-cm to 150-cm. The ability to pass the traditional electrophysiology therapeutic and diagnostic catheters and instruments as well as larger, more innovative, instruments through a catheter introduced with a small outside diameter is derived from the ability to atraumatically expand the distal end of the catheter or sheath to create a larger through lumen to access the cardiac chambers. The ability to pass multiple catheters through a single sheath with a single septal penetration is inherently safer and less time-consuming than a multiple septal puncture procedure. The expandable distal end of the catheter can comprise between 5% and 95% of the overall working length of the catheter. The proximal end of the catheter is generally larger than the distal end to provide for pushability, torqueability (preferably approximately 1:1 torqueability), steerability, control, and the ability to easily pass large diameter instruments therethrough. In an embodiment, the sheath can be routed to its destination over one or more already placed guidewires with a diameter ranging from 0.010 inches up to 0.040 inches and generally approximating 0.035 inches in diameter. An advantage of approaching the treatment site by the veins, instead of the arteries, is that the venous pressure is lower than that in the arterial system, thus reducing the potential for catastrophic hemorrhage during the procedure.

Another embodiment of the invention comprises an endovascular access system for providing minimally invasive access to atrial structures of the mammalian heart. The system includes an access sheath comprising an axially elongate tubular body that defines a lumen extending from the proximal end to the distal end of the sheath. At least a portion of the distal end of the elongate tubular body is expandable from a first, smaller cross-sectional profile to a second, greater cross-sectional profile. In an embodiment, the first, smaller cross-sectional profile is created by making axially oriented folds in the sheath material. These folds may be located in only one circumferential position on the sheath, or there may be a plurality of such folds or longitudinally oriented crimps in the sheath. The folds or crimps may be made permanent or semi-permanent by heat-setting the structure, once folded. In an embodiment, a releasable or expandable jacket is carried by the access sheath to restrain at least a portion of the elongate tubular structure in the first, smaller cross-sectional profile during insertion and up to or during inflation of the distal region. In another embodiment, the jacket is removed prior to inserting the sheath into the patient. In an embodiment, the elongate tubular body is sufficiently pliable to allow the passage of objects having a maximum cross-sectional size larger than an inner diameter of the elongate tubular body in the second, greater cross-sectional profile. The adaptability to objects of larger dimension is accomplished by pliability or re-shaping of the cross-section to the larger dimension in one direction accompanied by a reduction in dimension in a lateral direction. The adaptability may also be generated through the use of malleable or elastomerically deformable sheath material. This re-shaping or non-round cross-section can be beneficial in passing two or more catheters through a single sheath with a minimum lateral cross-sectional area.

In another embodiment of the invention, a transluminal access sheath assembly for providing minimally invasive access comprises an elongate tubular member having a proximal end and a distal end and defining a working inner lumen. In this embodiment, the tubular member comprises a folded or creased sheath that can be expanded by a dilatation balloon. The dilatation balloon, if filled with fluids, preferably liquids and further preferably radiopaque liquids, at appropriate pressure, can generate the force to radially dilate or expand the sheath. The dilatation balloon is removable to permit subsequent instrument passage through the sheath. Longitudinal runners may be disposed within the sheath to serve as tracks for instrumentation, which further minimize friction while minimizing the risk of catching the instrument on the expandable plastic tubular member. Such longitudinal runners are preferably circumferentially affixed within the sheath so as not to shift out of alignment. In yet another embodiment, the longitudinal runners may be replaced by longitudinally oriented ridges and valleys, termed flutes. The flutes, or runners, can be oriented along the longitudinal axis of the sheath, or they can be oriented in a spiral, or rifled, fashion.

In many of the embodiments, the proximal end of the access assembly, apparatus, or device is preferably fabricated as a structure that is flexible, resistant to kinking, and further retains both column strength and torqueability. Such structures include tubes fabricated with coils or braided reinforcements and preferably comprise inner walls that prevent the reinforcing structures from protruding, poking through, or becoming exposed to the inner lumen of the access apparatus. Such proximal end configurations may be single lumen, or multi-lumen designs, with a main lumen suitable for instrument, guidewire, endoscope, or obturator passage and additional lumens being suitable for control and operational functions such as balloon inflation. Such proximal tube assemblies can be affixed to the proximal end of the distal expandable segments described heretofore. In an embodiment, the proximal end of the catheter includes an inner layer of thin polymeric material, an outer layer of polymeric material, and a central region comprising a coil, braid, stent, plurality of hoops, or other reinforcement. It is beneficial to create a bond between the outer and inner layers at a plurality of points, most preferably at the interstices or perforations in the reinforcement structure, which is generally fenestrated. Such bonding between the inner and outer layers causes a braided structure to lock in place. In another embodiment, the inner and outer layers are not fused or bonded together in at least some, or all, places. When similar materials are used for the inner and outer layers, the sheath structure can advantageously be fabricated by fusing of the inner and outer layer to create a uniform, non-layered structure surrounding the reinforcement. The polymeric materials used for the outer wall of the jacket are preferably elastomeric to maximize flexibility of the catheter. The polymeric materials used in the composite catheter inner wall may be the same materials as those used for the outer wall, or they may be different. In another embodiment, a composite tubular structure can be co-extruded by extruding a polymeric compound with a stent, braid, or coil structure embedded therein. The reinforcing structure is preferably fabricated from annealed metals, such as fully annealed stainless steel, titanium, or the like. In this embodiment, once expanded, the folds or crimps can be held open by the reinforcement structure embedded within the sheath, wherein the reinforcement structure is malleable but retains sufficient force to overcome any forces imparted by the sheath tubing.

In an embodiment of the invention, it is beneficial that the sheath comprise a radiopaque marker or markers. The radiopaque markers may be affixed to the non-expandable portion or they may be affixed to the expandable portion. Markers affixed to the radially expandable portion preferably do not restrain the sheath or catheter from radial expansion or collapse. Markers affixed to the non-expandable portion, such as the catheter shaft of a balloon dilator can be simple rings that are not radially expandable. Radiopaque markers include shapes fabricated from malleable material such as gold, platinum, tantalum, platinum iridium, and the like. Radiopacity can also be increased by vapor deposition coating or plating metal parts of the catheter with metals or alloys of gold, platinum, tantalum, platinum-iridium, and the like. Expandable markers may be fabricated as undulated or wavy rings, bendable wire wound circumferentially around the sheath, or other structures such as are found commonly on stents, grafts, stent-grafts, or catheters used for endovascular access in the body. Expandable radiopaque structures may also include disconnected or incomplete surround shapes affixed to the surface of a sleeve or other expandable shape. Non-expandable structures include circular rings or other structures that completely surround the catheter circumferentially and are strong enough to resist expansion. In another embodiment, the polymeric materials of the catheter or sheath may be loaded with radiopaque filler materials such as, but not limited to, bismuth salts, or barium salts, or the like, at percentages ranging from 1% to 50% by weight in order to increase radiopacity. The radiopaque markers allow the sheath to be guided and monitored using fluoroscopy.

In order to enable radial or circumferential expansive translation of the reinforcement, it may be beneficial not to completely bond the inner and outer layers together, thus allowing for some motion of the reinforcement in translation as well as the normal circumferential expansion. Regions of non-bonding may be created by selective bonding between the two layers or by creating non-bonding regions using a slip layer fabricated from polymers, ceramics or metals. Radial expansion capabilities are important because the proximal end needs to transition to the distal expansive end and, to minimize manufacturing costs, the same catheter may be employed at both the proximal and distal end, with the expansive distal end undergoing secondary operations to permit radial or diametric expansion.

In another embodiment, the distal end of the catheter is fabricated using an inner tubular layer, which is thin and lubricious. This inner layer is fabricated from materials such as, but not limited to, FEP, PTFE, polyamide, polyethylene, polypropylene, Pebax, Hytrel, and the like. The reinforcement layer comprises a coil, braid, stent, or plurality of expandable, foldable, or collapsible rings, which are generally malleable and maintain their shape once deformed. Preferred materials for fabricating the reinforcement layer include but are not limited to, stainless steel, tantalum, gold, platinum, platinum-iridium, titanium, nitinol, and the like. The materials are preferably fully annealed or, in the case of nitinol, fully martensitic. The outer layer is fabricated from materials such as, but not limited to, FEP, PTFE, polyamide, polyethylene, polypropylene, polyurethane, Pebax, Hytrel, and the like. The inner layer is fused or bonded to the outer layer through holes in the reinforcement layer to create a composite unitary structure. The structure is crimped radially inward to a reduced cross-sectional area. A balloon dilator is inserted into the structure before crimping or after an initial crimping and before a final sheath crimping. The balloon dilator is capable of forced radial, or diametric, expansion of the reinforcement layer, which provides sufficient strength necessary to overcome any forces imparted by the polymeric tubing, thus controlling the cross-sectional shape of the polymeric tubing. The dilator is also capable of overcoming any forces imparted by tissues, including atrial or even ventricular myocardial tissue, through which the sheath is inserted.

Another embodiment of the invention comprises a method of providing endovascular access to the left atrium. The method first comprises percutaneously placing a hollow needle into the femoral vein, inserting a guidewire through the hollow needle into the vein, withdrawing the needle, and inserting a sheath with a tapered obturator into the puncture site and into the vein over the guidewire. The guidewire is next withdrawn, as is the tapered obturator and a 0.032 to 0.035-inch stiff guidewire is advanced into the vein and to the level of the right atrium or superior vena cava (SVC) through the inferior vena cava (IVC). A radially expandable sheath is next advanced into the femoral vein and advanced to the right atrium over the guidewire. The expandable sheath is articulated at its distal end so that it is turned toward and positioned against the Foramen Ovale of the atrial septum. The guidewire is next withdrawn and replaced with a Brockenbrough-type needle, which is advanced through the guidewire lumen of the expandable sheath. The Brockenbrough-type needle is advanced through the atrial septum into the left atrium while maintaining the expandable sheath in position against the septal wall, either by normal cardiac movement or by mechanical forward force on the Brockenbrough needle. The expandable sheath is next advanced axially through the septal wall, over the Brockenbrough-type needle and the needle, affixed to its control wire is withdrawn from the proximal end of the expandable sheath. A dilator, positioned within the expandable sheath is next radially expanded causing the distal end of the sheath to expand radially so as to dilate the hole in the tissues of the atrial septum. The dilator is, next, deflated and removed form the sheath, leaving a large central lumen for the passage of instruments into the left atrium. The expanded sheath is capable of holding a single instrument or multiple instruments of, for example, 8 to 10 French diameter. Suitable hemostatic and anti-reflux valves and seals are affixed the distal end of all devices except guidewires to ensure maintenance of hemostasis and prevention of air entry into the vasculature. Following therapeutic or diagnostic procedures, or both, the sheath is withdrawn from the patient allowing the septal puncture to close, thus preventing communication of blood between the right and left atrium. Throughout substantially the entire procedure, heparinized saline or other anti-thrombogenic solution is infused through an infusion port operably connected to an infusion line at the proximal end of the sheath. The infusion line is operably connected to the central lumen of the sheath, generally in the region of the hub, and the infused fluid flows out through the distal end of the sheath. In another embodiment, the distal end of the expandable portion of the sheath comprises a plurality of fenestrations or holes so that the infused fluid can exit the sheath through these holes. The infusion of this fluid is beneficial in minimizing thrombosis within or about the sheath as well as minimizing the occurrence of thromboemboli that might be generated by a sheath in the venous or arterial circulation.

In many embodiments, the expandable access sheath is configured to bend, or flex, around sharp corners and be advanced into the right atrium so that the longitudinal axis of its distal end is perpendicular to the atrial septal wall. Provision can optionally be made to actively orient or steer the sheath through the appropriate angles of between 20 to 120 degrees or more and to bend in one or even two planes of motion. The steering mechanism, in various embodiments, can be a curved guidewire and straight catheter, curved catheter and straight guidewire, a movable core guidewire, or a combination of the aforementioned. The expandable sheath also needs to be able to approach the right atrium from a variety of positions. In one embodiment, radial expansion of the distal end of the access sheath from a first smaller diameter cross-section to a second larger diameter cross-section is next performed, using a balloon dilator. The balloon dilator is subsequently removed from the sheath to permit passage of instruments that may not normally have been able to be inserted into the atrium of the heart. Once the sheath is in place, the guidewire may be removed or, preferably, it may be left in place. The atrial septum is gently dilated with radial force, preferably to a diameter of 10 mm or less, rather than being axially or translationally dilated by a tapered dilator or obturator. In most embodiments, the use of the expandable trans-septal sheath eliminates the need for multiple access system components.

In another embodiment of the invention, the expandable sheath comprises steerable members that eliminate the need for a 0.038-inch guidewire to be placed prior to sheath insertion and advancement. In another embodiment, the Brockenbrough-type needle, or septal penetrator, is integrated into the expandable sheath so that it can be used to puncture the atrium but does not need to be advanced and withdrawn through the sheath. The integral septal penetrator is actuated by the operator at the proximal end of the sheath. The controls at the proximal end of the sheath are operably connected to the septal penetrator at the distal end of the sheath by linkages, pressure lumens, electrical lines, or the like, embedded within the sheath and routed from the proximal end to the distal end. The septal penetrator is capable of bending with the articulating sheath distal region. In yet another embodiment, a reversible fixation device, or safety cushion, is provided at the distal end of the expandable sheath. The reversible fixation device is actuated by the operator at the proximal end of the sheath. The controls at the proximal end of the sheath are operably connected to the fixation device at the distal end of the sheath by linkages, pressure lumens, electrical lines, or the like, embedded within the sheath and routed from the proximal end to the distal end. The reversible fixation device can be an inflatable structure such as a balloon, a moly-bolt expandable structure, an expandable mesh, an umbrella, or the like, preferably positioned to expand within the left atrium. In an embodiment, the structure of the catheter or sheath is such that it is able to maintain a selectively rigid operating structure sufficient to provide stability against the atrial septum to support the advancement of trans-septal needles or penetrators. The sheath can be selectively stiffened, at least at its distal end, to provide a non-deflecting platform for support of instrumentation, such as the septal penetrator, which is passed therethrough.

In another embodiment of the invention, the proximal end of the expandable sheath comprises hemostasis or backflow check seals or valves to prevent blood loss and retrograde flow of air into the circulatory system. The hub of the sheath comprises such hemostasis seal. The seal comprises an annular soft elastomeric gasket that seals against catheters, instruments, and the dilator, inserted therethrough. The seal can further comprise a valve such as a stopcock, one-way valve such as a duckbill or flap valve, or the like to prevent significant blood loss and air entry when an instrument or catheter is removed from the lumen of the expandable sheath. The soft annular seal can further comprise a mechanism to compress the inner diameter of the seal radially inward, such as the mechanisms found on Tuohy-Borst valves. The hub further comprises one or more sideport for injection of contrast media such as Omnipaque, Renografin, or other Barium-loaded solutions, for example, or anticoagulant solutions such as heparin, coumadin, persantin, or the like, or for the measurement of pressure at or near the distal end of the sheath. The dilator hub comprises a central lumen with a Tuohy-Borst valve and one or more sideports for balloon inflation, said sideports operably connected to lumens in the dilator catheter for injection or withdrawal of fluids from a balloon at the distal end of the dilator and optionally for measurement of pressure at or near the dilator distal end. The dilator hub can also comprise a slide knob, a trigger, or other lever to actuate a septal puncture device at the distal end of the dilator. The dilator hub, the sheath hub, or both, can also comprise a handle, lever, or trigger mechanism to enable steering mechanisms at the distal end of the dilator, the sheath, or both, respectively.

The expandable sheath, in an embodiment, comprises radiopaque markers to denote the beginning and end of the expandable region, and the middle of the expandable region. The middle of the expandable region is useful in that it can be aligned with the atrial septum during the sheath expansion procedure. The sheath can comprise radiopaque materials such as gold wire, platinum wire, tantalum wire, or coatings of the aforementioned over a malleable, stainless steel, deformable reinforcing layer. Such complete radiopaque markings are especially useful for sheath dilation insofar as they allow the operator to more clearly visualize the extent to which the sheath has been dilated once the dilator is activated. In a preferred embodiment, a radiopaque marker band is affixed to the dilator substantially near the distal tip of the dilator so that the position of the distal tip can be observed and controlled relative to the wall of the left atrium or other cardiac structures. This radiopaque marker band can be a non-expandable, axially elongate tubular structure that is adhered to the non-expandable dilator shaft. Another non-expandable radiopaque marker band can be adhered to the dilator shaft at a position substantially corresponding to the proximal most dilating portion of the dilator or sheath. Another non-expandable radiopaque marker band can be adhered to the dilator shaft at a position substantially corresponding to the distal most dilating portion of the dilator or sheath. Thus, the atrial septum can be positioned with confidence between the two dilator radiopaque markers and dilation will be assured. The radiopaque marker bands can further be configured to appear different under fluoroscopy, for example by making the distal tip marker a single band, the distal dilation marker two bands, and the proximal dilator marker, three bands. Yet another configuration of radiopaque marker bands can be achieved by using malleable wire windings of gold, tantalum, platinum alloys, or the like, which are embedded within the folded and expandable sheath, preferably at or near the distal end of the sheath and, optionally, at or near the proximal end of the expandable portion of the sheath. These wire windings can expand with the sheath and can help show the extents of the sheath even after the dilator has been removed.

Since in many embodiments the hub of a Trans-Septal sheath requires many hemostasis valves and fluid input connectors or ports, the hub can be a longer structure than that on current guide catheters. Therefore, it may be required that a longer Brockenbrough needle is used to allow sufficient working length to provide for maneuverability within the cardiac anatomy. It may be beneficial to use Brockenbrough needles, which are longer than the standard 60-71 cm length, preferably those of 80 to 90 cm in length. Furthermore, the sheath hub length can be advantageously foreshortened by use of tightly grouped ports and minimum length Tuohy-Borst valves as well as "Y" connectors that are integrated into the hub, rather than being separately attached. Thus, the working length of the entire system is between 50 and 90 cm and preferably between 60 and 80 cm. The sheath hub length, including the length of the dilator hub, is between 3 and 15 cm and preferably between 4 and 8 cm, the preferred length being appropriate if a shorter 70-cm or 71-cm long Brockenbrough needle is used. In an embodiment, the hub of the dilator comprises a "Y" or "T" connector operably connected to the guidewire lumen of the hub. The guidewire access port is controlled by and comprises a hemostasis valve or seal such as Tuohy-Borst connector. The side port is generally a luer port, luer lock port, or similar and is controlled by a stopcock, valve, Tuohy-Borst valve or other device to prevent unwanted fluid (including air) flow into or out of the guidewire port. The side port is beneficial in that it can be affixed to and operably connected to an infusion line for infusion of heparinized saline or other antithrombogenic material into the guidewire lumen of the sheath dilator. Such infusion of antithrombogenic fluid into the guidewire port during the procedure can help minimize thrombosis and thromboemboli generation.

In order to facilitate maneuvering the expandable trans-septal sheath into the right atrium and through the atrial septum, as well as for support of the sheath during catheter passage therethrough, it is beneficial in many embodiments to impart a curve into the trans-septal sheath, and optionally through the dilator. This curve is preferably a bend of between 20 to 120 degrees and preferably between 30 and 90 degrees. The bend can be in one plane or it can be in two orthogonal planes. An exemplary bend is to bend the sheath approximately 45 degrees out of plane 1 and approximately 50 degrees out of line in plane 2, which is orthogonal to plane 1. The radius of the curve can range between 2-cm and 12-cm and preferably between 3-cm and 10-cm in each of the two directions. Another example is a single plane curve of 90 degrees with a radius of around 3-cm to 12-cm. These bends are preferably imparted to the distal region of the non-expandable sheath tubing, just proximal to the expandable region. The bends can also be imparted through the expandable region but maintaining those bends in the expandable region may further require the use of a bent or curved shaped balloon, a resilient longitudinal support within the expandable region, a bent or curved dilator shaft, or both. The bending can be imparted to the tubing by placing the tubing over a curved mandrel and then heat-setting the tubing while over the mandrel. The tubing needs to be heated above glass-transition temperature, which is preferably above body temperature (37 degrees centigrade) for the heat set to be optimal. Materials used in the heat settable region can include, but not be limited to, polyethylene, PEN, PET, polyamide, polyimide, PEBAX, Hytrel, and the like. The expandable region of a trans-septal sheath need not be long and ranges between 0.5-cm and 20-cm with a preferred length of between 1-cm and 10-cm. By keeping the expandable region short, the region of the sheath comprising the bend, a bend, which makes the sheath have properties similar to those of a guiding catheter, is not in the expandable region, although methodologies of maintaining a bend within the expandable region are disclosed herein.

In yet another embodiment, the exterior of the sheath, and optionally the internal lumen of the sheath, can be coated with a lubricious coating comprising materials such as, but not limited to, silicone oil or a hydrophilic hydrogel comprising polyethylene glycol, polyether polyurethane, or the like.

In another embodiment, the proximal end of the sheath comprises a non-circular interior cross-section. The interior cross-section of the sheath can be oval, or it can comprise two or more completely walled off or partially walled off separate lumens. The sheath hub, which is affixed to the non-expandable proximal end of the sheath, can comprise two or more separate instrumentation ports, each of which are operably connected to a lumen or partial lumen within the sheath and which can advantageously comprise hemostasis valves. The instrumentation ports are especially useful for passage of, for example, multiple electrophysiology catheters, a mapping catheter and a therapeutic catheter, a ring catheter and an ablation catheter, or the like. Segregation of the multiple instrumentation can be useful to prevent binding or interference between the multiple catheters or instruments passed through the sheath. In yet another embodiment, the proximal end of the sheath has a non-circular cross-section that minimizes the overall cross-sectional area or circumference of a sheath configured to accept two or more catheters. This non-circular cross-section can be an oval, ellipse, rounded triangle, or the like. The non-circular cross section can, for example, reduce an 18 French OD catheter to around 15.5 French, using the same wall thickness and still retain the capability to accept two 8 French catheters within its internal lumen or lumens. Reduction in exterior cross-section is clearly useful in making the procedure as minimally invasive as possible and may make a procedure, which normally takes a cutdown, a percutaneous procedure.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 17A illustrates a side view of a collapsed, non-expanded trans-septal sheath, according to an embodiment of the invention;

FIG. 17B illustrates a side view of an expanded trans-septal sheath, according to an embodiment of the invention;

FIG. 17C illustrates a side view of an expanded trans-septal sheath with the dilator removed, according to an embodiment of the invention;

DETAILED DESCRIPTION OF THE PREFERRED EMBODIMENTS

Figure 21A:
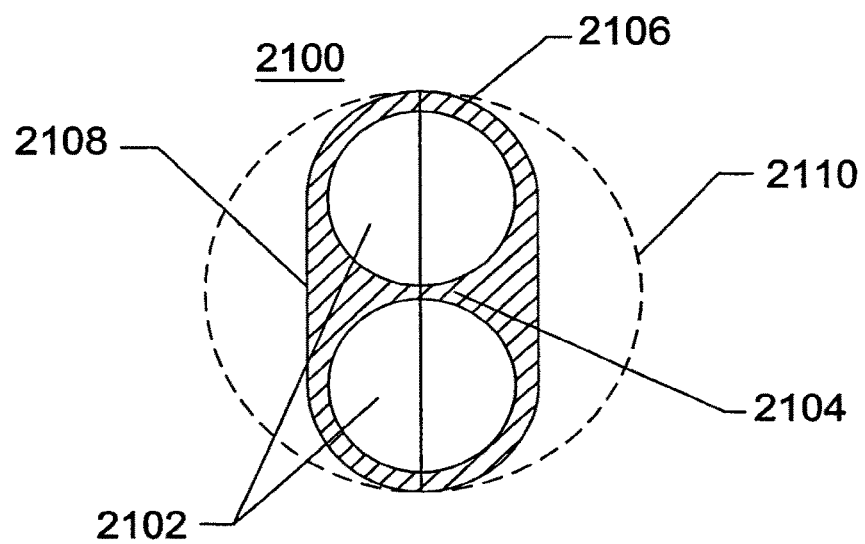
FIG. 21A illustrates an embodiment of a lateral cross-sectional profile of a proximal end of a sheath comprising a non-circular outer profile and a dual partial lumen inner profile, according to an embodiment of the invention.
Figure 21B:
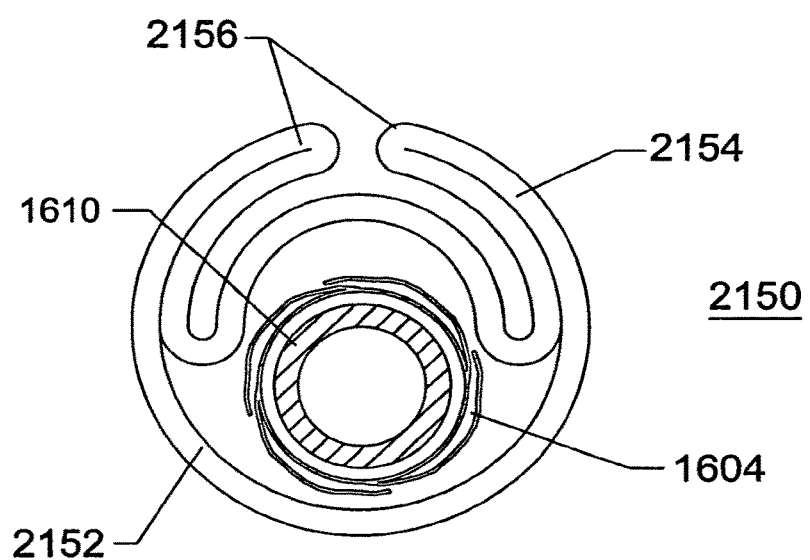
FIG. 21B illustrates an embodiment of a lateral cross-sectional profile of the folded, compressed, expandable distal region of the sheath, according to an embodiment of the invention.

FIG. 21B illustrates an embodiment of a lateral cross-sectional profile of the folded, compressed, expandable distal region of the sheath, according to an embodiment of the invention. The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

In the description herein the terms catheter or sheath will be used to refer to being an axially elongate hollow tubular structure having a proximal end and a distal end. The structure can have any cross-sectional shape but in most embodiment the structure has a circular cross-sectional shape. The axially elongate structure further has a longitudinal axis and has an internal through lumen that extends from the proximal end to the distal end for the passage of instruments, fluids, tissue, or other materials. The axially elongate hollow tubular structure is generally flexible and capable of bending, to a greater or lesser degree, through one or more arcs in one or more directions perpendicular to the main longitudinal axis. As is commonly used in the art of medical devices, the proximal end of the device is that end that is closest to the user, typically a cardiologist, surgeon, or electrophysiologist. The distal end of the device is that end closest to the patient or that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter in mm and is often useful for catheters that have non-circular cross-sectional configurations. While the original measurement of "French" used π (3.14159 . . . ) as the conversion factor between diameters in millimeters (mm) and French, the system has evolved today to where the conversion factor is 3.0.

Figure 1:
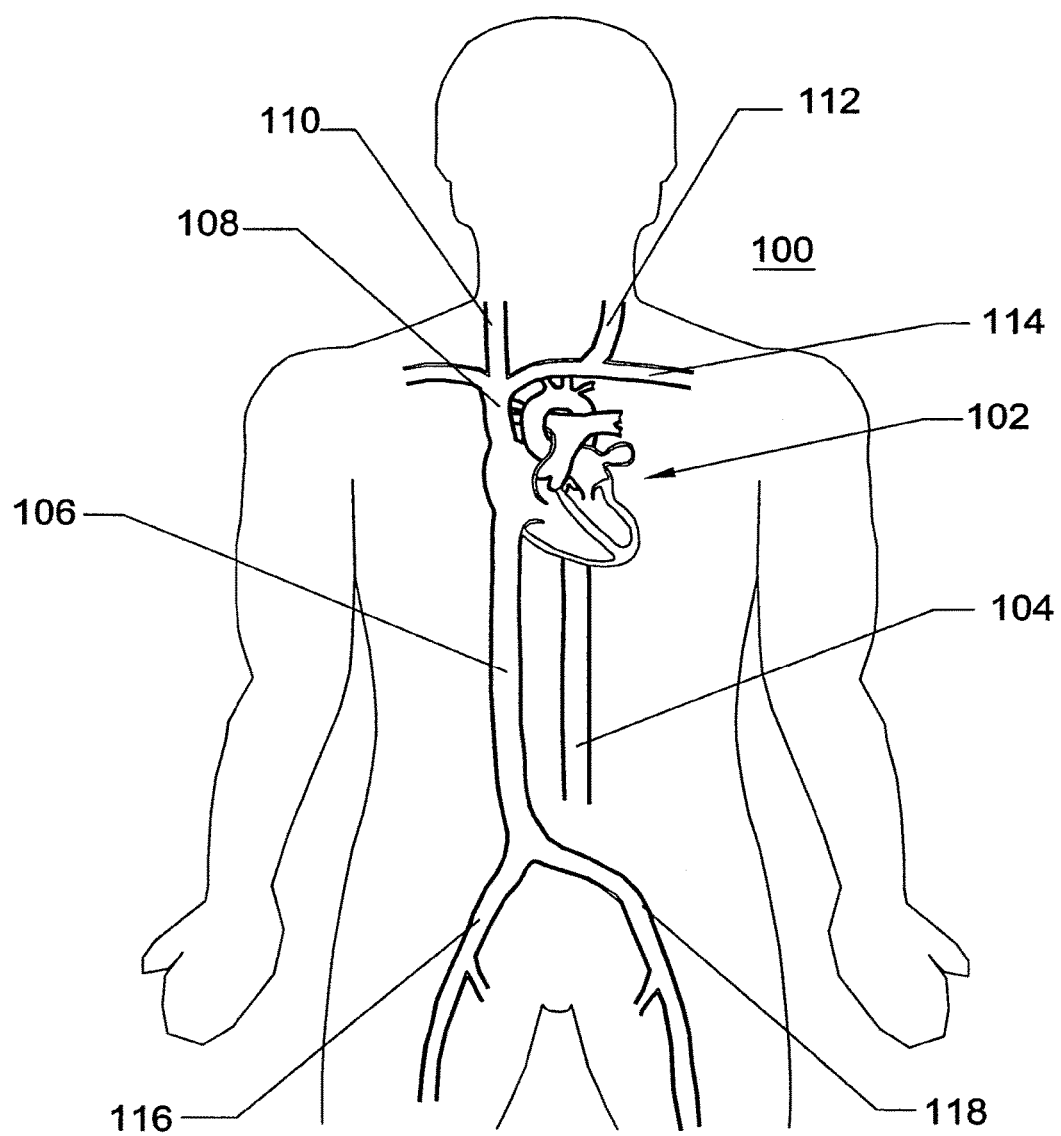
FIG. 1 is a front view schematic representation of the human venous circulatory system including the heart and the great veins.

FIG. 1 is a schematic frontal (anterior) illustration (looking posteriorly) of a human patient 100 comprising a heart 102, a descending aorta 104, an inferior vena cava 106, a superior vena cava 108, a right jugular vein 110, a left jugular vein 112, a subclavian vein 114, a right femoral vein 116 and a left femoral vein 118. In this illustration, the left anatomical side of the body of the patient 100 is toward the right of the illustration. FIG. 1 primarily illustrates components of the venous circulation.

Referring to FIG. 1, the heart 102 is a pump, the outlet of which is the aorta, including the descending aorta 104, which is a primary artery in the systemic circulation. The circulatory system, which is connected to the heart 102 further comprises the return, or venous, circulation. The venous circulation comprises the superior vena cava 108 and the inferior vena cava 106, which return blood from the upper extremities and lower extremities, respectively. The right and left jugular veins, 110 and 112, respectively, and the subclavian vein 114 are smaller venous vessels with venous blood returning to the superior vena cava 108. The right and left femoral veins, 116 and 118 respectively, return blood from the legs to the inferior vena cava 106. The veins carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from left ventricle of the heart 102 to the tissues of the body. The pressures within the arteries for a normal person undulate, with a modified triangle waveform, between a diastolic pressure of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of 300 mm Hg can occur in extremely hypertensive persons.

Figure 2:
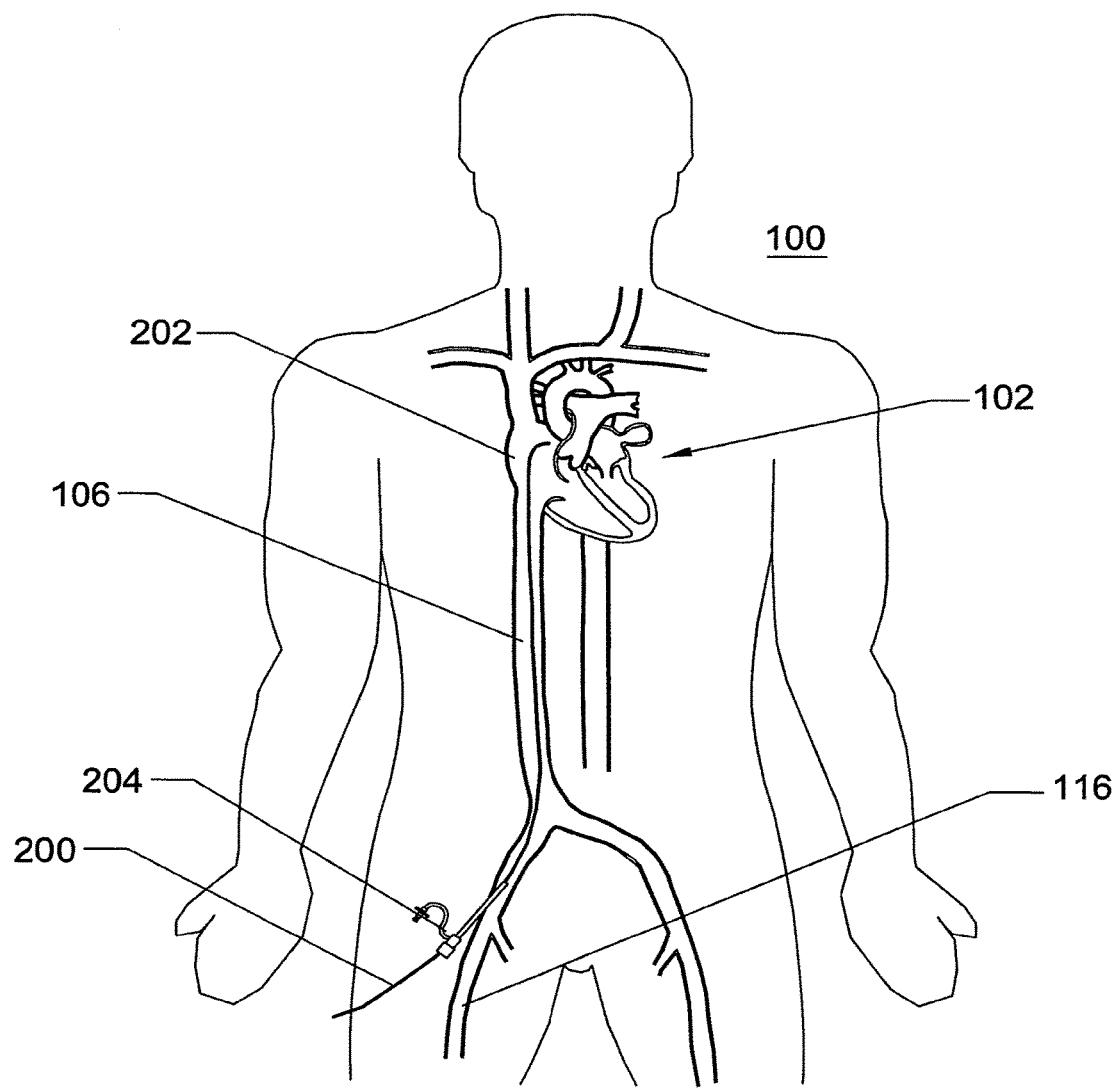
FIG. 2 is a front view schematic representation of the human venous circulatory system with a guidewire routed from the femoral vein into the right atrium.

FIG. 2 is a schematic frontal illustration, looking posteriorly from the anterior side, of the patient 100. A vascular introduction sheath 204 has been inserted into the right femoral vein 116 via a percutaneous puncture or incision. A guidewire 200 has been inserted through the introduction sheath 204 and routed, cranially, up the inferior vena cava 106 to the right atrium 202, one of the chambers of the heart 102. In this illustration, the left anatomical side of the patient 100 is toward the right. The guidewire 200 has been placed so that it can be used to track therapeutic or diagnostic catheters into a region of the heart 102.

Referring to FIG. 2, the venous circulation, through which the guidewire 200 has been routed, is generally at lower pressure between 0 and 20 mm Hg than is the systemic circulation, of which the descending aorta is a part. The pressure within the systemic circulation may range from 60 to over 300 mm Hg depending on the level of hypertension or hypotension existent in the patient. By accessing the heart through the venous circulation, the chance of hemorrhage from the catheter insertion site is minimized, as is the demand on the hemostasis valves built into any catheters used on the patient.

Figure 3:
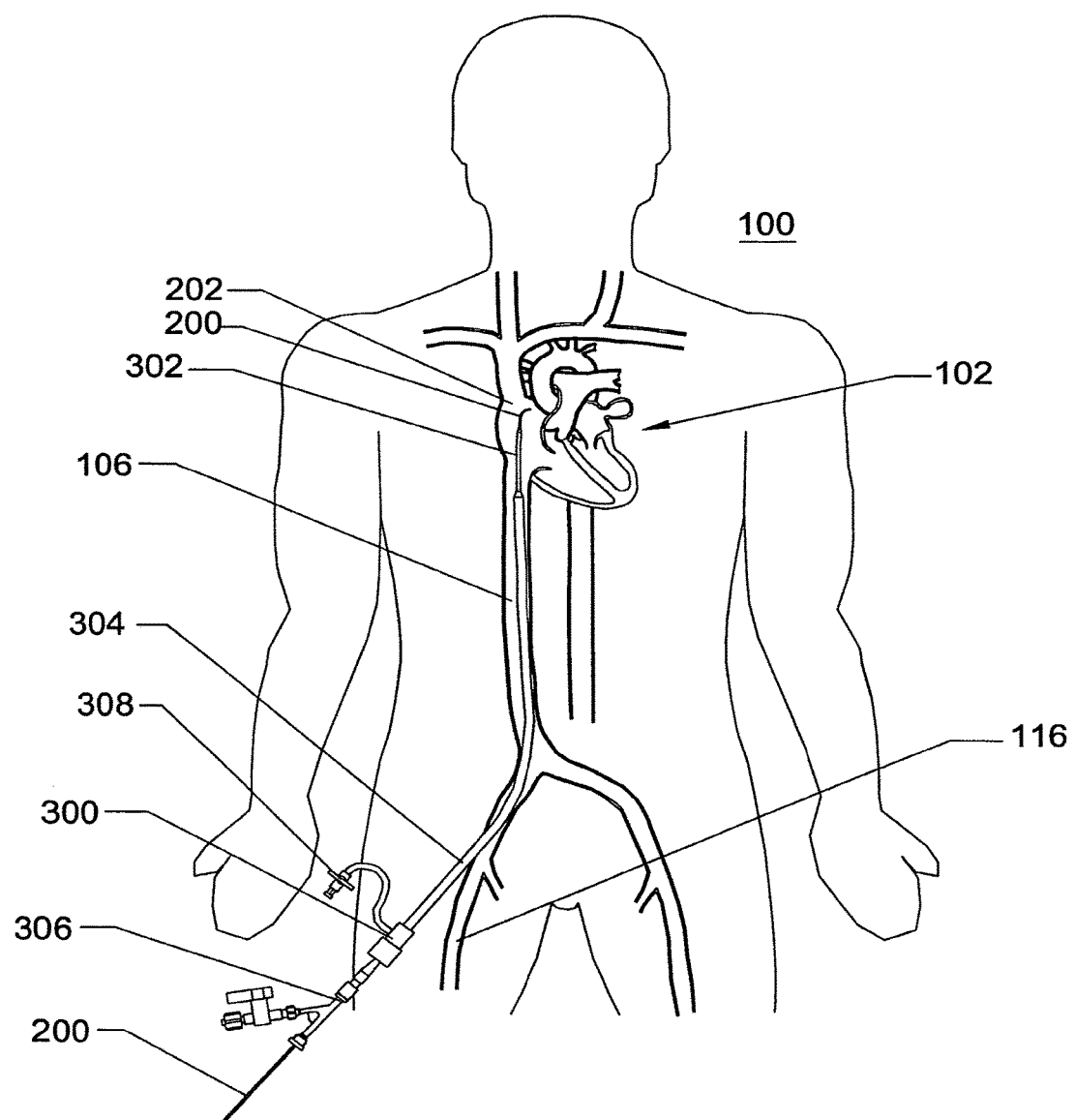
FIG. 3 is a front view schematic representation of the human venous circulatory system with an expandable sheath advanced into the right atrium, according to an embodiment of the invention.

FIG. 3 is a frontal illustration, looking posteriorly from the anterior side, of the patient 100. The vascular introduction sheath 204 of FIG. 2 has been removed from the right femoral vein 116 and a larger Trans-Septal Expandable Sheath 300 having certain features and advantages according to the present invention has been inserted into the venous circulation over the guidewire 200 and routed through the inferior vena cava 106 into the right atrium 202 of the heart 102. The expandable trans-septal sheath 300 further comprises a dilator 306, the proximal most part of which is shown in FIG. 3. The expandable trans-septal sheath 300 further comprises a proximal non-expandable region 304 and a distal expandable region 302.

Referring to FIG. 3, the venous circulation is filled with blood (not shown) that is somewhat depleted of oxygen and enriched with carbon dioxide as a result of interaction with body tissues. In the illustrated embodiment, the expandable region 302 of the expandable trans-septal sheath 300 is smaller in diameter than the proximal non-expandable region 304.

Figure 4:
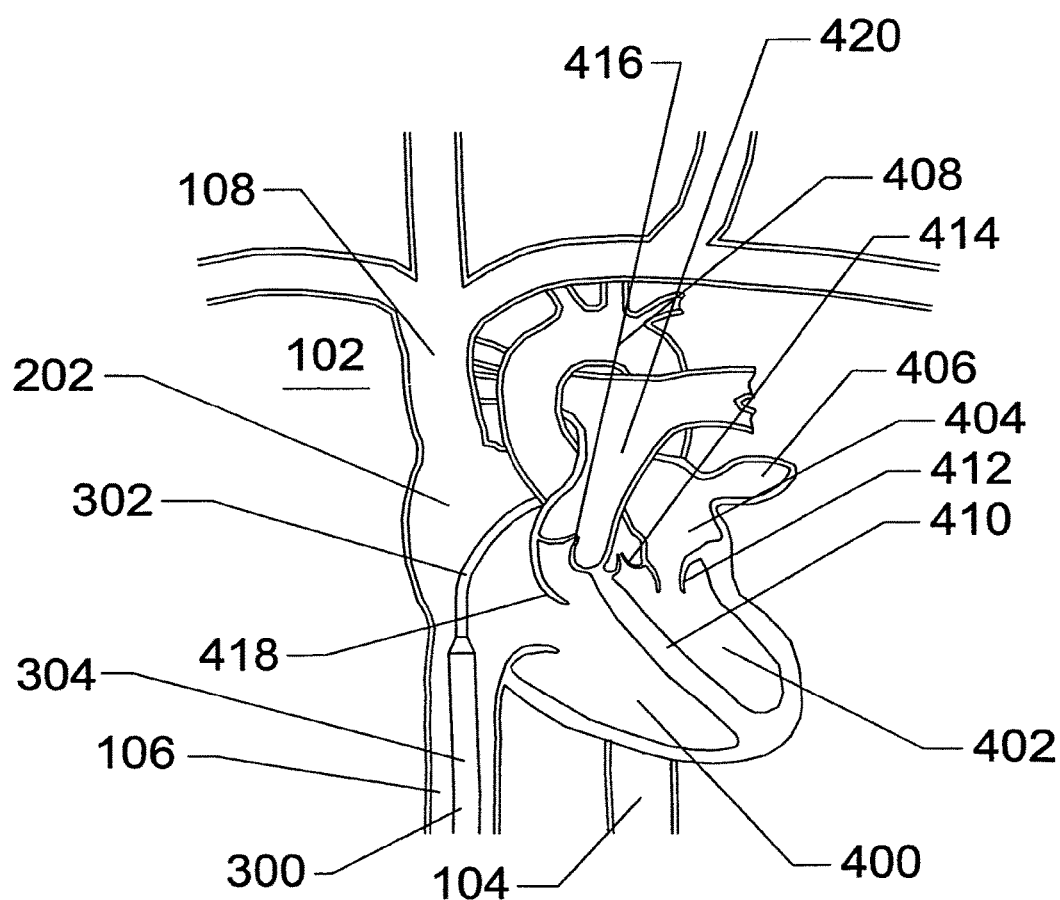
FIG. 4 is a cross-sectional illustration of the heart with the expandable sheath articulated and positioned within the right atrium and the guidewire removed, according to an embodiment of the invention.

FIG. 4 is a cross-sectional illustration of the heart 102, further comprising the descending aorta 104, the inferior vena cava 106, the superior vena cava 108, the right atrium 202, a right ventricle 400, a left ventricle 402, a left atrium 404, and a left atrial appendage 406. The heart 102 also comprises an aortic arch 408, a ventricular septum 410, a mitral valve 412, an aortic valve 414, a pulmonary valve 416, a tricuspid valve 418, and a pulmonary artery 420. The expandable region 302 of the sheath 300 is visible in the right atrium 202 and the proximal non-expandable region 304 of the expandable trans-septal sheath 300 is visible in the inferior vena cava 106.

Referring to FIG. 4, the expandable distal region 302 has been articulated or deflected in an arc so that its distal end rests against the atrial septum (not shown), the wall of myocardium that divides the right atrium from the left atrium. In this illustration, the atrial septum is obscured by the ascending aorta 602 (FIG. 6), that region of aorta between the aortic arch 408 and the aortic valve 414, as well as the pulmonary artery 420 and the pulmonary valve 416. The distal end of the distal sheath region 302 is positioned so that it rests within the Foramenal valley of the atrial septum, a naturally thin area of the atrial septum and a preferred landmark for continuing the procedure. The distal region 302 can be articulated, in an embodiment, with the use of an integral or removable internal steering mechanism. The distal region 302, in another embodiment, can be articulated using a movable core guidewire or a bent guidewire (not shown) inserted through the central lumen of the distal region 302 of the sheath 300.

Figure 5:
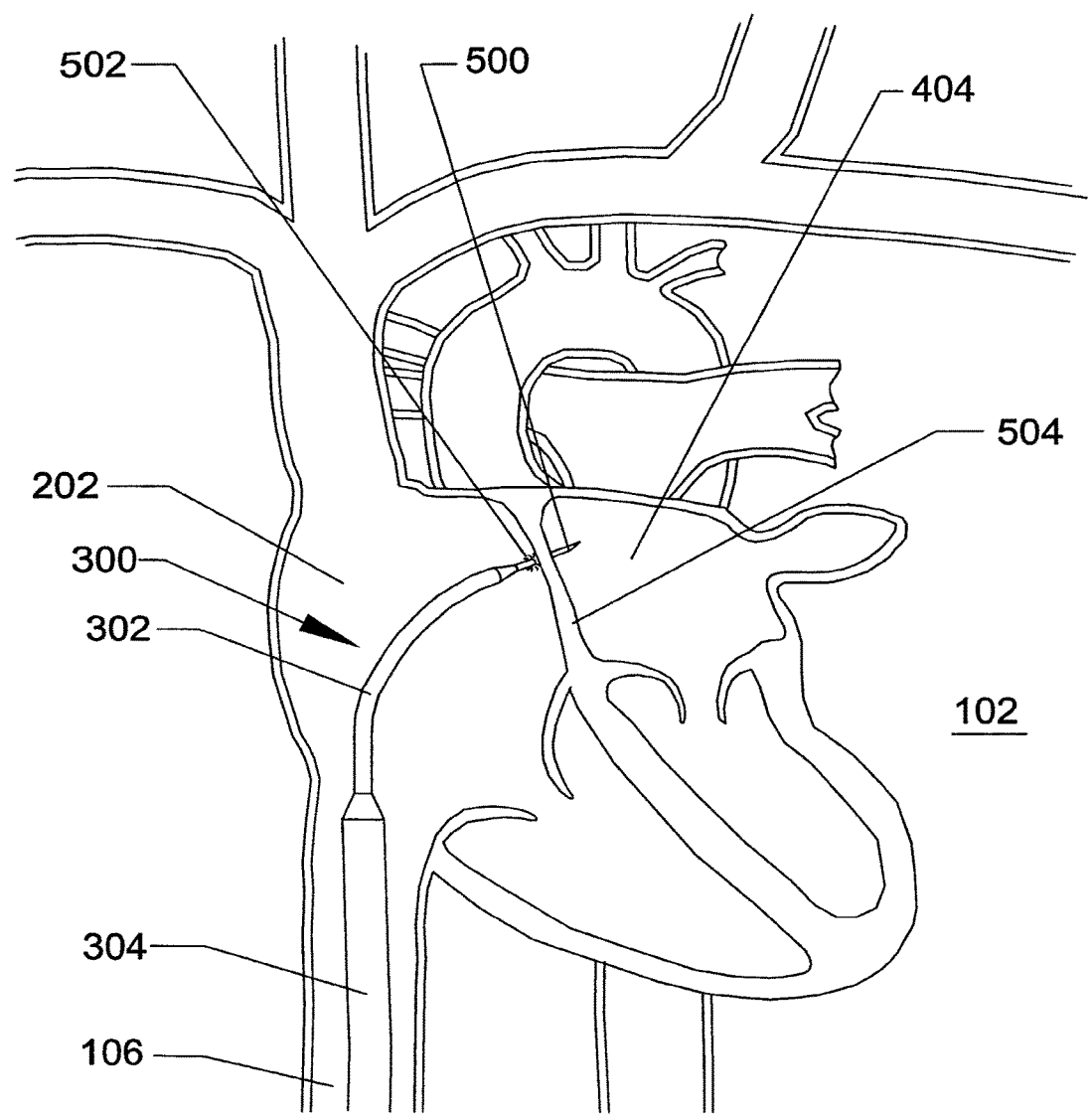
FIG. 5 is a cross-sectional illustration of the heart with the expandable sheath positioned at the atrial septum and the septal penetrator advanced across the atrial septum into the left atrium, according to an embodiment of the invention.

FIG. 5 is a cross-sectional illustration of the heart 102, showing the atrial septum 504. The ascending aorta 602 (FIG. 6), aortic valve 414, pulmonary artery 420, and pulmonary valve 416 of FIG. 4 have been removed from this illustration for clarity and to show the atrial septum 504. The distal expandable region 302 of the sheath 300, substantially located within the right atrium 202, is shown with its long axis perpendicular to the atrial septum 504. The proximal end 304 of the sheath 300 is shown resident within the inferior vena cava 106. A septal penetrator 500 is shown extended through a puncture 502 in the atrial septum 504 and is routed into the left atrium 404.

Referring to FIG. 5, the septal penetrator 500 is a needle or axially elongate structure with a sharp, pointed distal end. The septal penetrator 500 is resident within the guidewire lumen of the dilator 306 (FIG. 3), which is removably resident within the distal expandable region 302. The septal penetrator 500 is actuated at the proximal end of the sheath 300. The septal penetrator 500 is operably connected to a control mechanism such as a button, lever, handle, trigger, etc., which is affixed, permanently or removably, at the proximal end of the dilator 306 by way of a linkage, pusher rod, electrical bus, or the like that runs the length of the dilator 306. The penetrator 500 can also be integrated into the sheath 300 but the removable dilator 306 is more advantageous. Care must be taken not to have the septal penetrator 500 pierce the wall of the left atrium 404 opposite the atrial septum 504 so length control and advance control are important as is guidance, either by fluoroscopy, MRI, ultrasound, or the like. Further care must be taken not to inadvertently pierce the aorta in the region upstream or anatomically proximal to the aortic arch 408 (FIG. 4). The distal expandable region 302 is bent, deflected, or articulated through an angle of between 30 and 120 degrees to achieve approximate perpendicularity with the atrial septum 504. The septal penetrator 500 can be solid, it may be hollow like a hypodermic needle, or it may have a "U" or "C"-shaped cross-section. The center or core of a hollow, "C", or "U"-shaped septal penetrator can be filled with a guidewire or other core element to prevent incorrect tissue penetration. The septal penetrator 500 can be rigid or it can be flexible but retain column strength. Such flexible configurations can comprise cutouts in the wall of the penetrator 500 or guidewire-like construction. The septal penetrator 500 can be initially straight or it can be initially curved. The septal penetrator 500 can be fabricated from shape memory material such as nitinol and heat treated to cause curving once the material is heated from martensitic to austenitic temperatures. Such heating can be performed using electrical heating, hot water injection, or the like. Preferred temperatures for the austenite finish temperature, in this application range from 25 degrees to around 42 degrees centigrade. Higher temperatures require more heating and rely on hysteresis to minimize the return to martensite when the heating temperature is removed.

Figure 6:
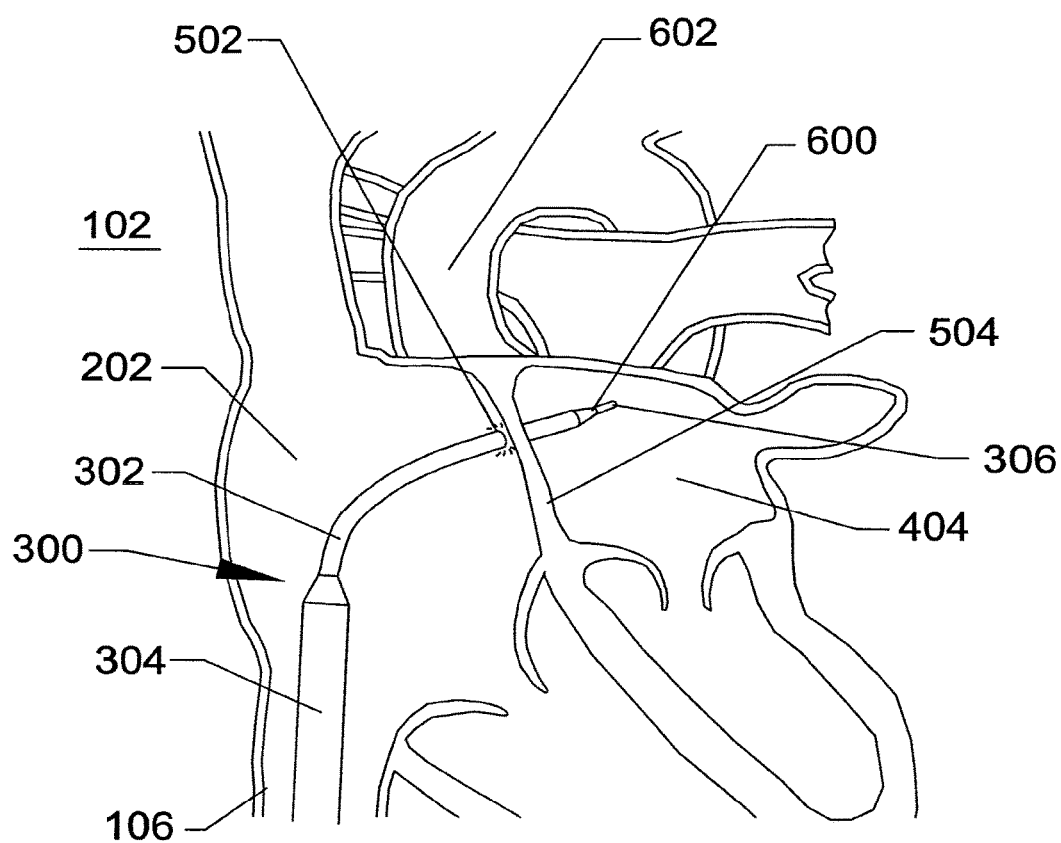
FIG. 6 is a cross-sectional illustration of the heart with the expandable sheath advanced into the left atrium across the atrial septum and the septal penetrator withdrawn into the dilator of the expandable sheath, according to an embodiment of the invention.

FIG. 6 illustrates a cross-sectional view of the heart 102 showing the distal expandable region 302 having been advanced across the atrial septum 504 from the right atrium 202 and into the left atrium 404. The tapered tip 600 of the dilator 306 leads the distal end of the expandable region 302 through the septal puncture 502 created by the penetrator 500. That region of the ascending aorta 602 that does not obscure this anterior view of the atrial septum 504 is shown. The proximal non-expandable region 304 has advanced, to follow the advancing distal expandable region 302, so that the proximal region 304 is located not only in the inferior vena cava 106 but also within the right atrium 202.

Referring to FIG. 6, the expandable access sheath 300 is pre-assembled with its internal dilator 306. The dilator 306 is, in an embodiment, a catheter with a dilatation balloon (not shown) affixed to a dilator shaft. The dilatation balloon is preferably an angioplasty-type, non-elastomeric balloon and is fabricated from materials such as, but not limited to, PET, polyamide, cross-linked polyolefins, or the like. The dilator shaft is terminated at its proximal end with an inflation port that is operably connected to a lumen within the dilator shaft. The lumen within the dilator shaft is operably connected to the interior of the balloon by way of scythes or other openings. The tapered tip 600 is affixed to the distal end of the dilator 306 and is fabricated from thermoplastic elastomer such as, C-Flex or from elastic polymers such as silicone elastomer, polyurethane, or the like. The tapered tip 600 can have a general funnel shape tapering from small at the distal end to large at the proximal end. In another embodiment, the tapered dilator tip 600 can have a complex taper with two or more angles and can also include intermediate cylindrical, non-tapered, regions. The tapered tip 600 can be made to expand with the distal end of the balloon and then shrink down with the balloon when it is deflated, facilitating withdraw through the lumen of the expanded distal region 302 of the sheath 300. The tapered tip 600 can be asymmetric to substantially match the cross-sectional configuration of an expandable sheath section that is folded and has inherently axial asymmetry. The tapered tip 600 can, in an embodiment, be elastomeric or resilient, to expand and compress with the balloon.

Figure 7:
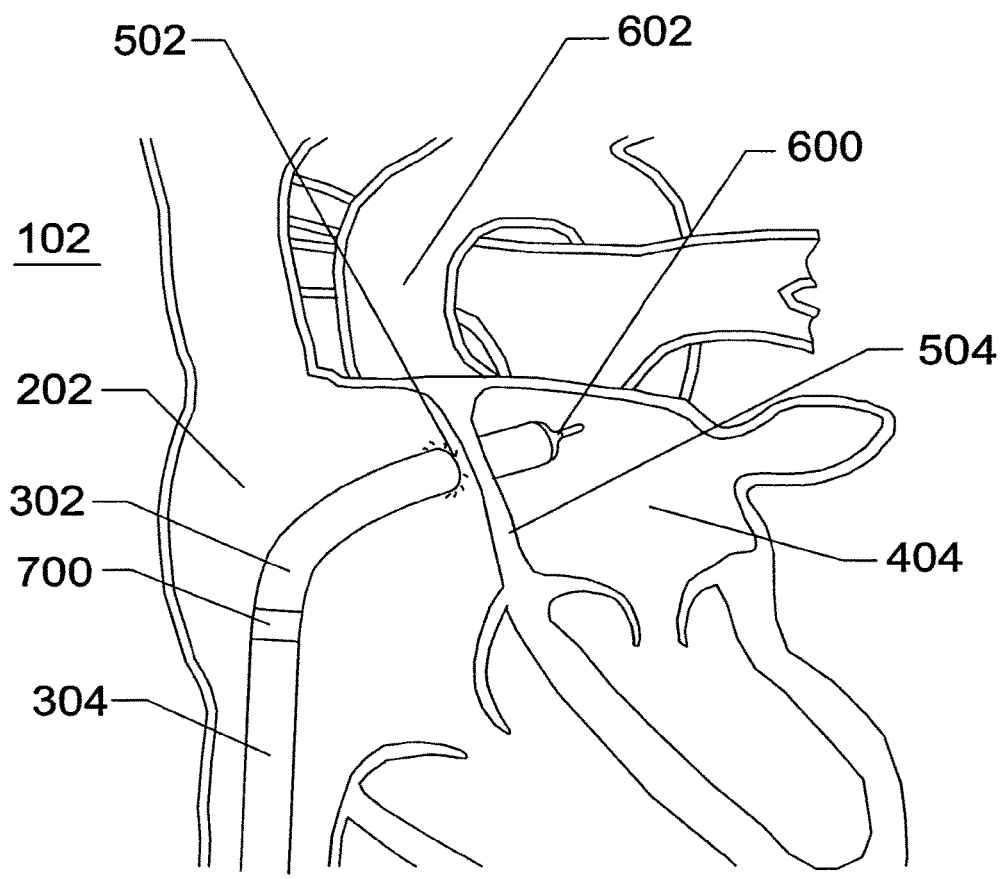
FIG. 7 is a cross-sectional illustration of the heart with the expandable sheath dilated at its distal end by the dilator, according to an embodiment of the invention.

FIG. 7 illustrates a cross-sectional view of the heart 102 showing the distal expandable region 302 having been radially expanded while placed across the atrial septum 504 between the right atrium 202 and the left atrium 404. The distal expandable region 302 is now generally of the same diameter as the proximal region 304. The transition zone 700 is that region connecting the distal region 302 and the proximal region 304. The dilator balloon resides within the transition zone 700 as well as the distal expandable region 302. The puncture 502 in the atrial septum 504 has now been dilated using radial dilation means and the distal end of the sheath 302 is resident within the left atrium 404. The dilator tip 600 remains within the left atrium 404. The use of radial dilation is considered beneficial and superior to translation dilation by tapered axially translating dilators with regard to tissue healing and wound closure. The radial dilation allows the septal transit to be performed with relatively small expandable tips in the range of 7 to 10 French. Following transit of the septum through the perforation created by the penetrator, a small sheath with a smooth, tapered, distal transition can be advanced readily through the penetration. The expandable region 302 can then be dilated radially, opening up the septal penetration to any size from 12 to 30 French. Such radially dilated openings are known to heal more completely, following removal of the instrument. In another embodiment, the expandable region 302 can be expanded by forcing an inner dilator (not shown) distally along the long axis of the sheath 300 to force the expandable region 302 to dilate diametrically. Such axial translation dilation can be generated by way of a pusher affixed to the inner dilator at its distal end and a handle or mechanical lever at the proximal end of the sheath 300. The expandable region 302 can be elastomeric or comprise one or more longitudinal folds, which cause the circumference, and thereby the diameter, to be small until dilated.

Figure 8:
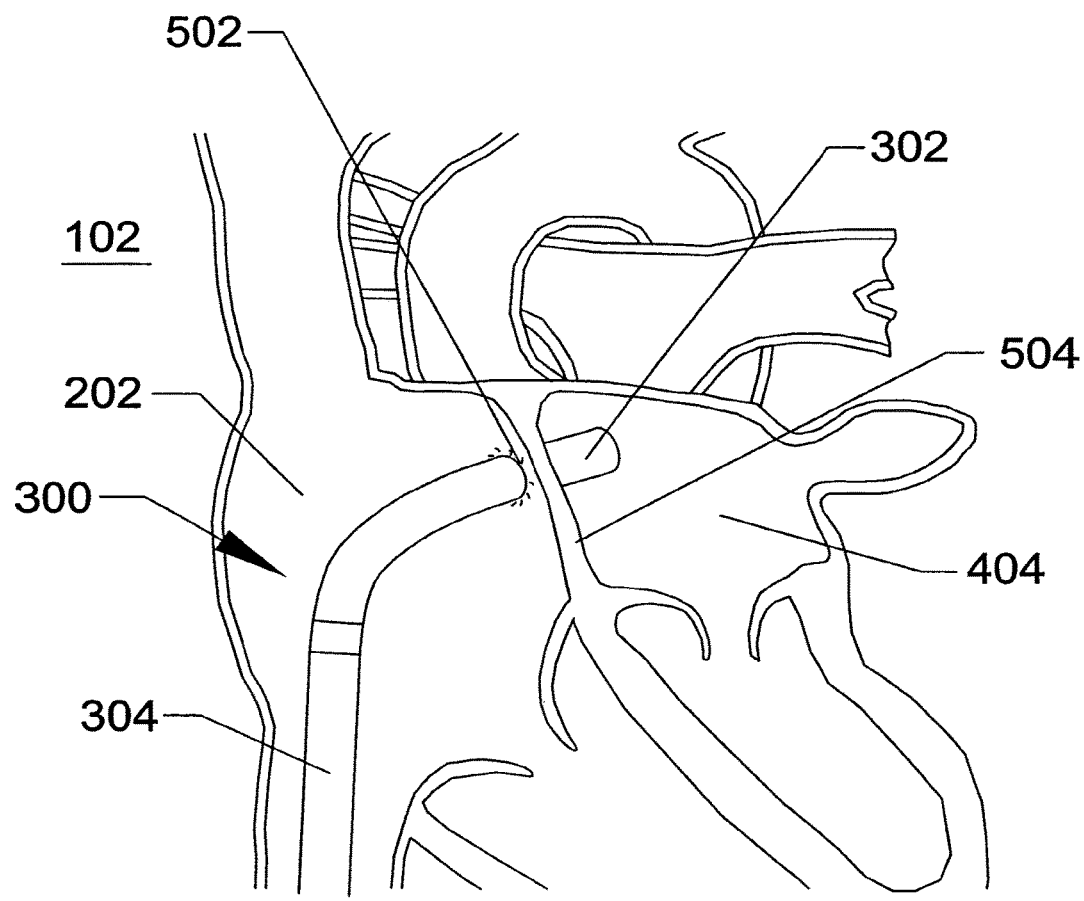
FIG. 8 is a cross-sectional illustration of the heart with the expandable dilator withdrawn from the sheath leaving a large central lumen for instrument passage into the left atrium, according to an embodiment of the invention.

FIG. 8 illustrates a cross-sectional view of the heart 102 wherein the distal end of the distal expandable region 302 is resident within the left atrium 404 and is located across the atrial septum 504. The tip 600 (FIGS. 6 and 7) of the dilator 306 (not shown) has been removed and withdrawn from the proximal end of the sheath 300. In this configuration, the sheath 300 retains a large, central lumen capable of passing instrumentation, catheters, or the like into the left atrium 404. The size of the sheath 300 is substantially the same whether in the distal expandable region 302 or the proximal non-expandable region 304. The central lumen of the sheath is exposed to pressure within the left atrium 404, said left atrial pressures being 20 mm Hg or less. This large sheath 300 is capable of delivering one, two, or more catheters into the left atrium 404 without the need for more than one atrial septal puncture 502.

Figure 9:
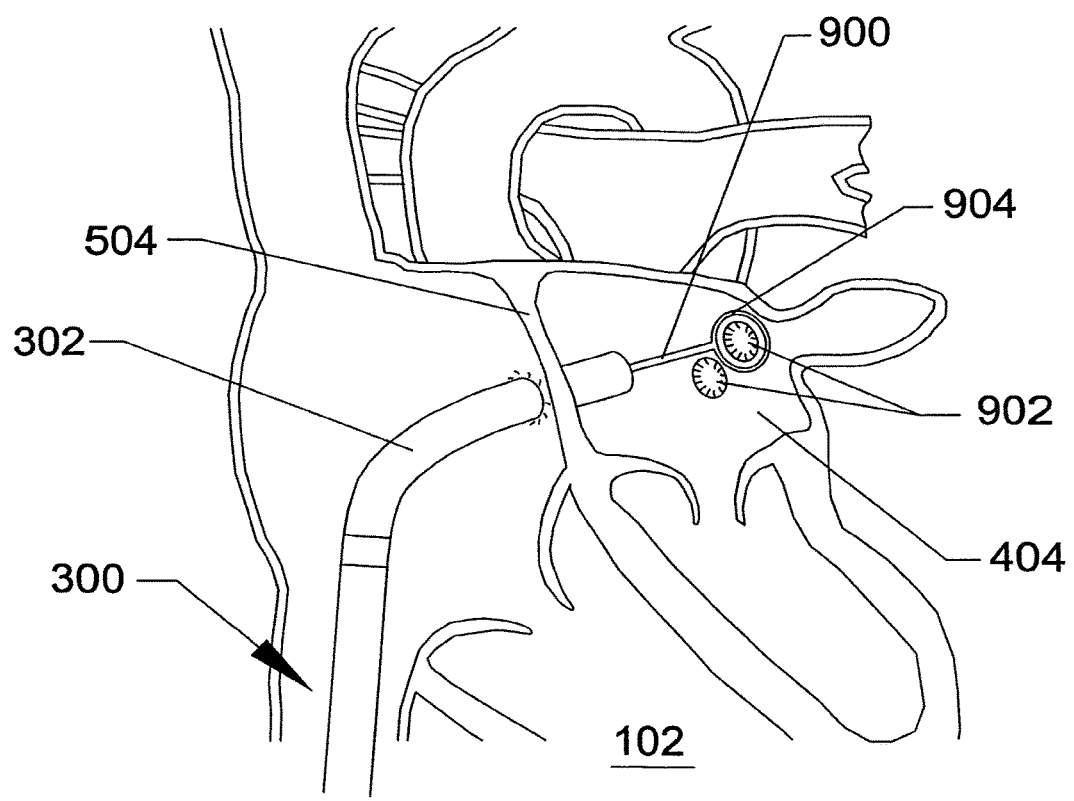
FIG. 9 is a cross-sectional illustration of the heart with an electrophysiology therapeutic catheter advanced through the central lumen of the expanded sheath into the left atrium, according to an embodiment of the invention.

FIG. 9 a cross-sectional view of the heart 102 wherein the distal end of the distal expandable region 302 is resident within the left atrium 404 and is located across the atrial septum 504. Two of the outlets for the pulmonary veins 902 are shown within the left atrium 404. The tissue around the pulmonary veins 902 is often a site for re-entrant waveforms that cause atrial arrhythmias. Ablation of this tissue using heat or extreme cold temperatures (cryogenics) can alleviate the arrhythmias. In the illustrated embodiment, an electrode 904 that emits Radiofrequency (RF) energy has been introduced at the end of an electrophysiology catheter 900 into the right atrium 404 through the expandable sheath 300. The electrode 904 shown is a round electrode called a lasso electrode and is capable of heating and ablating a ring of tissue in a single operation. Single point electrodes 904 can create line or ring ablations but must be drawn slowly along the tissue to ablate the desired pattern. Such electrode movement is difficult to achieve at the end of a curved 100-cm long, or longer, catheter being monitored by fluoroscopy or ultrasound. The heating electrodes can deliver energies such as microwaves, radio frequencies, high-intensity focused ultrasound (HIFU), and the like. Because these ring electrodes 904 are large in diameter, they may be advantageously placed through very large sheaths such as the expandable trans-septal sheath 300.

Figure 10:
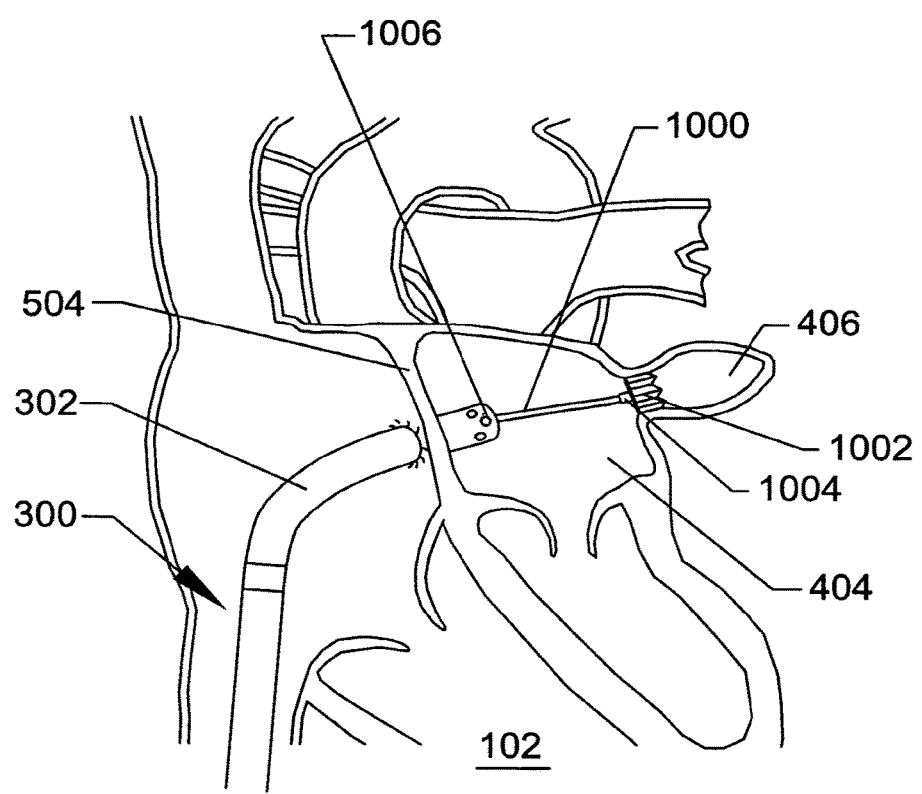
FIG. 10 is a cross-sectional illustration of the heart with an atrial septal plug delivery catheter advanced through the central lumen of the expanded sheath into the left atrium, according to an embodiment of the invention.

FIG. 10 illustrates a cross-sectional view of the heart 102 wherein the distal end of the distal expandable region 302 of the expandable trans-septal sheath 300 is resident within the left atrium 404 and is located across the atrial septum 504. A delivery catheter 1000 for an implantable device 1002 is routed through the expandable sheath 300. In this embodiment, the implantable device 1002 is an expandable plug capable of closing off the opening between the left atrium 404 and the left atrial appendage 406. The implantable device 1002 is releasably affixed to the distal end of the catheter 1000 by a releasable coupler 1004, activated by a linkage extending between the distal coupler 1004 and the proximal end of the delivery catheter 1000. Such left atrial appendage 406 plugs or filters have been shown to reduce emboli generation by the left atrial appendage 406 in conditions where the left atrium 404 is in a state of atrial fibrillation, or uncoordinated muscle contraction. Atrial fibrillation, while not life threatening, results in reduced cardiac output and exercise tolerance. It is also associated with a high rate of cerebrovascular embolic stroke. Left atrial appendage implants 1002 are radially collapsible during delivery. They are generally delivered through 14 French or larger catheters and a radially expandable delivery sheath would be advantageous. The trans-septal sheath 300 further comprises a plurality of ports, holes, fenestrations, or scythes 1006 near the distal end of the sheath 300. The holes 1006 penetrate through the sheath 300 from the outside to the inside and operably connect the central lumen (not shown) of the expandable region 302 to the environment outside the sheath 300. Fluid administered through the proximal end of the sheath 300 can exit these holes 1006 as well as through the open distal end of the sheath 300. It is beneficial to infuse fluids such as heparinized saline or other antithrombogenic fluid so as to minimize the risk of thrombus buildup within or around the sheath 300 as well as to minimize the risk of thromboemboli generation within the cardiovascular system. In another embodiment, the holes 1006 can be located anywhere on the sheath 300, including the non-expandable proximal end.

Figure 11:
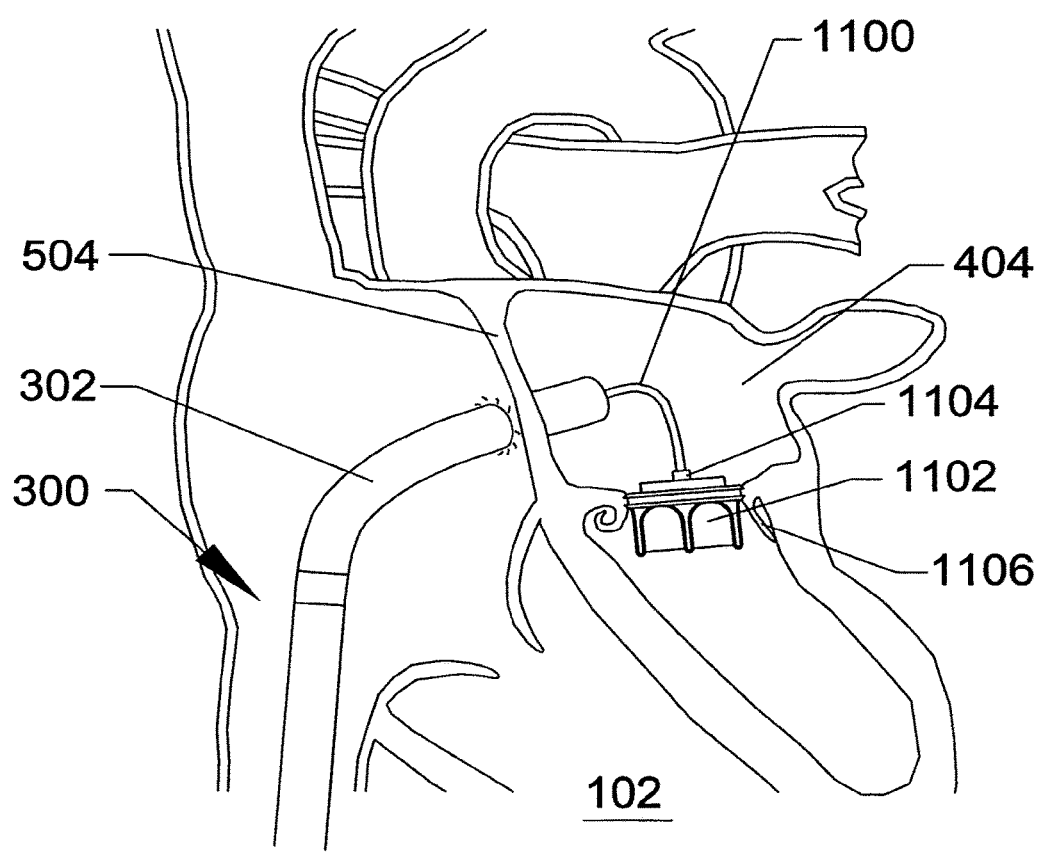
FIG. 11 is a cross-sectional illustration of the heart with a collapsible mitral valve prosthesis delivery catheter advanced through the central lumen of the expanded sheath into the left atrium, according to an embodiment of the invention.

FIG. 11 illustrates a cross-sectional view of the heart 102 wherein the distal end of the distal expandable region 302 of the expandable trans-septal sheath 300 is resident within the left atrium 404 and is located across the atrial septum 504. A mitral valve implant delivery catheter 1100 is routed through the expandable sheath 300. The catheter 1100 is controllably, releasably, affixed to the inlet side of a collapsible, mitral valve prosthesis 1102 by a coupler 1104. The coupler 1104 is operably connected to the proximal end of the delivery catheter 1100 by a linkage. The delivery catheter 1100 is required to articulate to reach the mitral valve orifice to place the mitral valve prosthesis 1102. The mitral valve prosthesis 1102 is expanded so that it engages the remnants of the diseased mitral valve leaflets 1106 so that it is secured in place. Such a prosthesis is necessarily large, (up to 35 mm diameter fully expanded) and requires a very large trans-septal catheter (20 to 30 French), even for a radially collapsed device. The expandable trans-septal catheter 300 would allow placement of such large devices with minimal damage to the atrial septum 504.

Figure 12:
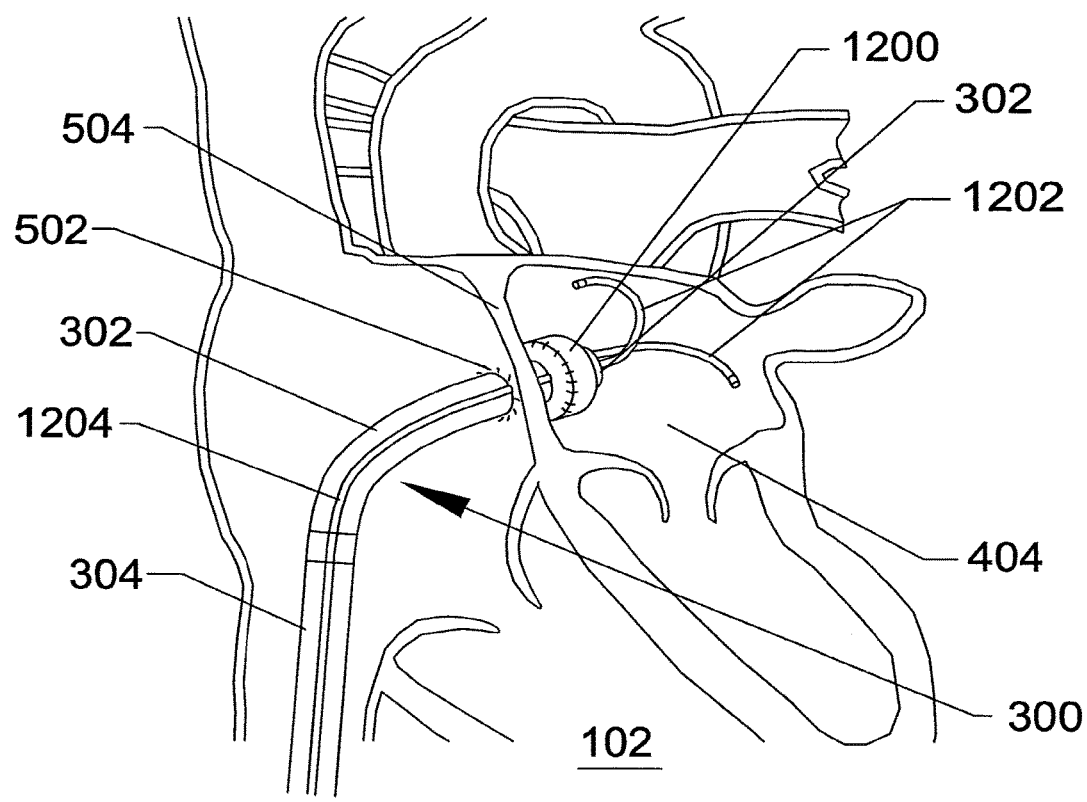
FIG. 12 is a cross-sectional illustration of the heart with the expandable sheath traversing into the left atrium and secured in place with a left atrial anchor system, according to an embodiment of the invention.

FIG. 12 illustrates a cross-sectional view of the heart 102 wherein the distal end of the distal expandable region 302 of the expandable trans-septal sheath 300 is resident within the left atrium 404 and is located across the atrial septum 504. A distal anchor 1200 is shown inflated within the left atrium 404 for the purpose of stabilizing the sheath 300 so that its expandable region 302 cannot be inadvertently pulled out of the left atrium 404. Two electrophysiology catheters 1202 are shown extending into the left atrium 404 out the distal end of the expandable region 302. An inflation lumen 1204 is illustrated riding on the surface of the sheath 300 in both the proximal region 304 and the distal expandable region 302. The inflation lumen 1204 is operably connected to an inflation port and valve at the proximal end of the sheath 300 and is operably connected to the interior of the distal anchor 1200. The distal anchor, in this embodiment, is a balloon. The balloon can be either non-compliant like an angioplasty balloon or compliant like a Foley balloon, the latter of which is fabricated from silicone elastomer, latex rubber, polyurethane, or the like. Non-compliant balloons can be made from cross-linked polyethylene or polypropylene or from stretch blow molded polyethylene terephthalate, polyamides, or the like. In another embodiment, a second balloon 1506 (FIG. 15) can be placed so that it expands within the right atrium 202 against the atrial septum 504. Inflation of the second balloon 1506 can be performed through the same inflation lumen 1204 as that used for the distal anchor 1200. Such inflation through the same inflation lumen 1204 would be substantially simultaneous with the distal anchor 1200. The second balloon 1506 would prevent distal migration of the sheath 300. In another embodiment, a dumbbell shaped balloon would replace the two separate balloons. The small diameter part of the dumbbell balloon is configured to reside within the puncture site 502. Such dumbbell balloon is preferably fabricated as a non-compliant balloon. The distal anchor could also be fabricated as a moly-bolt, umbrella, expandable braid, or other expandable structure activated by a linkage to the proximal end of the sheath. Fabrication of the distal anchor is achieved using materials such as, but not limited to, polyolefins such as polyethylene or polypropylene, polyamide, polyurethane, polyester, elastomeric materials, Hytrel, Pebax, or the like.

Figure 13:
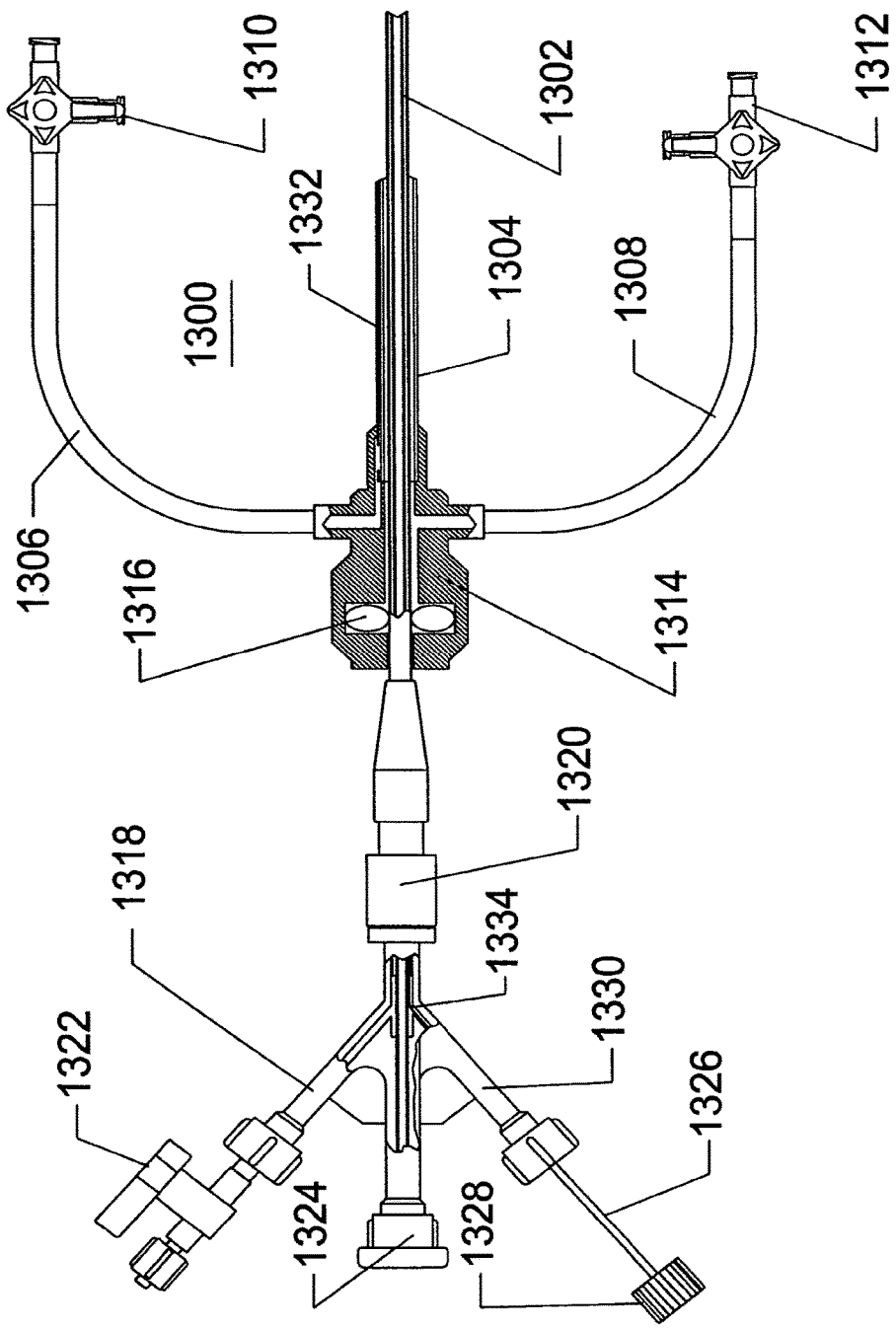
FIG. 13 is a cross-sectional illustration of the expandable sheath showing the proximal sheath and dilator hubs along with various hemostasis valves, actuators, and seals, according to an embodiment of the invention.

FIG. 13 illustrates a longitudinal cross-section of the proximal end 1300 of an embodiment of an expandable trans-septal sheath system that can be used as described above. The proximal end 1300 comprises a dilator shaft 1302, a sheath shaft 1304, an anchor inflation line 1306, a fluid infusion line 1308, an anchor line stopcock 1310, a fluid infusion valve 1312, a sheath hub 1314, a sheath valve 1316, a dilator inflation port 1318, a dilator hub 1320, a dilation stopcock 1322, a guidewire port valve 1324, a penetrator shaft 1326, a penetrator knob 1328, a penetrator spring (not shown), a penetrator access port 1330, an anchor inflation lumen 1332, and a penetrator linkage 1334.

Figure 14:
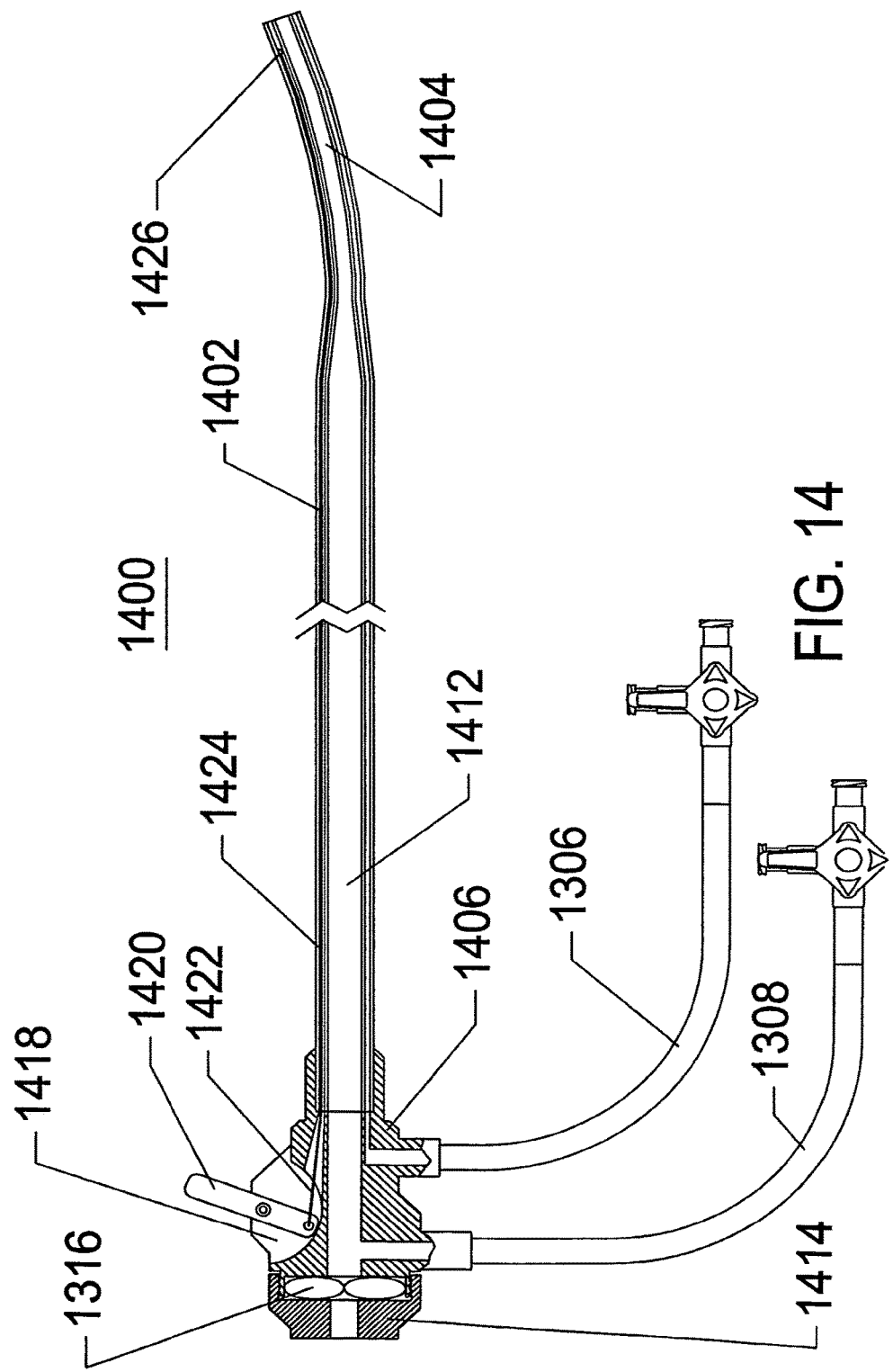
FIG. 14 is a cross-sectional illustration of the expandable sheath showing a deflection mechanism, according to an embodiment of the invention.

FIG. 14 illustrates a longitudinal cross-section of an articulating expandable trans-septal sheath 1400. The articulating, expandable sheath 1400 further comprises a proximal region 1402, a distal expandable region 1404, a sheath hub 1406, a transition zone 700, a central lumen 1412, a steering linkage lumen 1424, an anchor inflation line 1306, a fluid infusion line 1308, a compression cap 1414, a variable valve element 1316, a lever support 1418, a steering lever 1420, a steering linkage 1422, and a steering linkage distal fixation point 1426. In this embodiment, the articulation is generated by tension or compression force in the steering linkage 1422 being applied to the fixation point 1426 affixing the steering linkage 1422 to the distal end of the distal expandable region 1404. The distal expandable region is flexible and can be made preferentially more flexible in the region just proximal to the distal fixation point 1426. The lever 1418 provides mechanical advantage and can be used with ratchets, locks, friction elements, or the like to restrict movement of the lever 1418 and consequently the linkage 1422 when manual pressure is removed. The distal end of the sheath 1400 is shown bent, or articulated, into an arc and the lever 1420 is correspondingly moved forward, relative to the hub 1406, to cause tension in the linkage 1422. A second lever support 1418, steering lever 1420, steering linkage 1422, distal fixation point 1426 and steering linkage lumen 1424 can be added, in another embodiment, to permit articulation of the distal region 1404 in a second direction.

Figure 15:
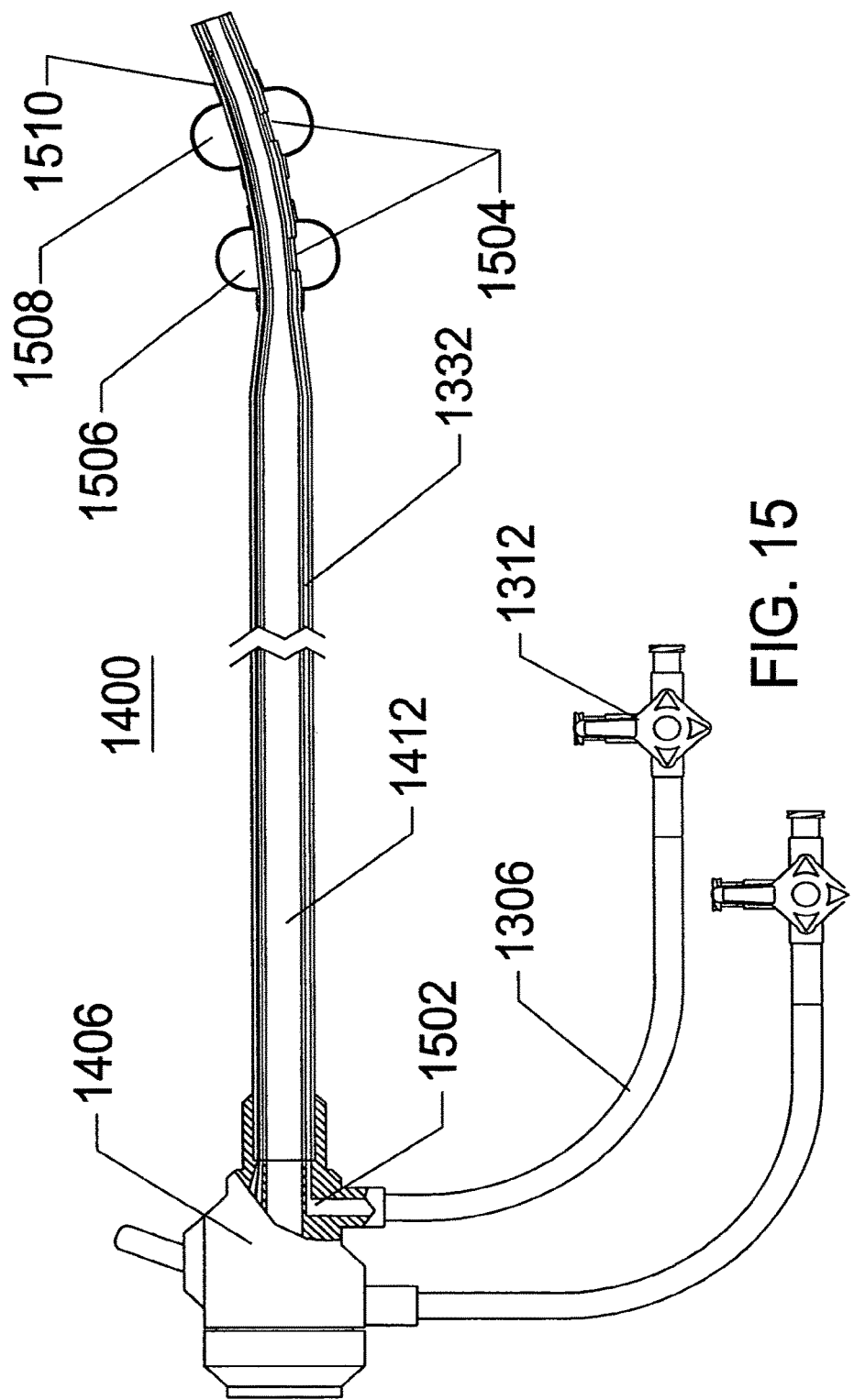
FIG. 15 is a cross-sectional illustration of the expandable sheath showing a distal anchor mechanism, according to an embodiment of the invention.

FIG. 15 illustrates a longitudinal cross-section of an articulating expandable sheath 1400 further comprising a distal anchor 1508, a proximal anchor 1506, and a plurality of anchor bonds 1510. The sheath 1400 further comprises an anchor inflation lumen 1332, a plurality of scythes 1504, an anchor inflation manifold 1502, an anchor inflation line 1306, an anchor inflation valve 1312, a hub 1406 and a central sheath lumen 1412. The distal anchor 1508 and the proximal anchor 1506 are shown as balloons that are inflated with fluid, preferably saline, water, or radiopaque contrast media. Inflation occurs through the anchor inflation valve 1312, the anchor inflation line 1306, the anchor inflation manifold 1502 within the hub 1406, and the anchor inflation lumen 1332, which are all operably connected. Fluid pressure is added or removed to the balloons 1506 and 1508 through the scythes 1504, which are holes or ports in the wall of the sheath 1400 that expose the region inside the distal anchor 1508 and proximal anchor 1506 to the fluid pressure of the anchor inflation lumen 1332.

Figure 16:
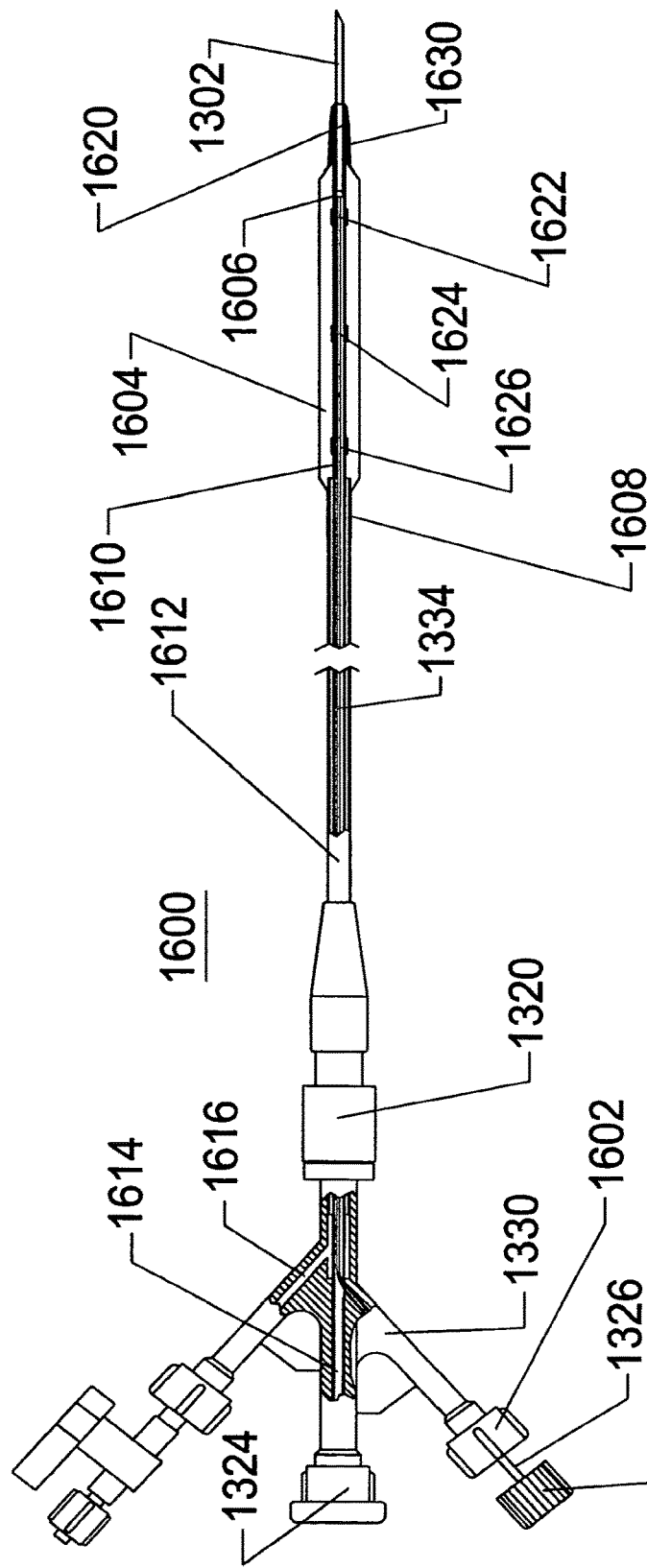
FIG. 16 is a cross-sectional illustration of the expandable sheath showing an atrial septal penetrator integral to the dilator, according to an embodiment of the invention.

FIG. 16 illustrates a longitudinal cross-section of a dilator 1600 suitable for use with the expandable trans-septal sheath 1400 (FIG. 15). The dilator 1600 further comprises a dilator hub 1320, a guidewire port with valve 1324, a penetrator access port 1330, a penetrator shaft 1326, a penetrator knob 1328, a penetrator spring (not shown), a penetrator linkage 1334, a penetrator 1302, a penetrator coupler 1606, a penetrator port closure 1602, an inner dilator tube 1610, an outer dilator tube 1612, a dilatation balloon 1604, a plurality of balloon bonds 1608, a distal fairing 1630, and a plurality of radiopaque markers 1620, 1622, 1624, 1626. The penetrator linkage 1334 and the penetrator 1302 can be solid, coiled, hollow tubes, or C-shaped. The C-shaped embodiment is capable of further accepting a guidewire in the guidewire lumen 1614 at the same time as the penetrator 1302 and penetrator linkage 1334. The spring (not shown) can be located between the penetrator knob 1328 and the penetrator port closure 1602 and allows the penetrator 1302 to be advanced temporarily and then retracted to its safety position automatically. The guidewire can serve the function of plugging a central hole or hollow within the penetrator 1302. The penetrator 1302 can be a curved or a straight needle, or it may be fabricated from shape memory materials such as nitinol and be configured to be inserted straight but bend upon exposure to Ohmic heating, body temperature, hot water flushed therethrough, or the like. The dilator balloon 1604 is preferably an angioplasty-type unfurling balloon with bonds at its proximal and distal end. The balloon 1604 is fabricated from high-strength materials such as, but not limited to, PET, polyamide, cross-linked polymers, polyethylene, and the like. The balloon 1604 and dilator 1600 can be fabricated to generate pressures of up to about 20 atmospheres without leakage or failure.

Referring to FIG. 16, the radiopaque markers 1620, 1622, 1624, and 1626 are all of the non-expandable type and are affixed to catheter or balloon tubing using adhesive, compression fit, interference fit, potting, overmolding, or the like. The radiopaque markers 1620, 1622, 1624, and 1626 are fabricated as short, axially elongate hollow cylinders using materials such as, but not limited to, platinum, gold, tantalum, iridium, barium, bismuth, or the like. The distal tip radiopaque marker 1620 is affixed over the balloon bond 1608 for ease of assembly and is generally covered by a distal shroud or fairing 1630. The radiopaque markers 1622, 1624 and 1626 are affixed to the inner tubing 1610 prior to attachment of the dilator balloon 1604. The radiopaque marker 1622 delineates the approximate distal end of the full diameter region of the dilatation balloon 1604. The radiopaque marker 1626 delineates the approximate proximal end of the full diameter region of the dilatation balloon 1604. The marker 1626 can also be positioned to correspond to the proximal end of the fully expandable portion of the sheath (not shown). The marker 1624 is generally optional and corresponds with the approximate center of the balloon 1604 or the expandable portion of the sheath (not shown). The inclusion of the radiopaque markers 1622, 1624, 1626 facilitates fluoroscopic visualization of the expandable portion of the sheath (not shown) or the dilatation balloon 1604 across the atrial septum to ensure correct positioning during sheath expansion. The distal marker 1620 facilitates fluoroscopic visualization of the distal tip of the dilator 1600 to ensure that it does not impinge on, perforate, or damage cardiac or other tissue structures within the body and that it follows the desired path within the patient. The distal fairing or shroud 1630 forms a gentle taper from the distal tip of the dilator and shields the distal edge of the sheath (not shown) so that the distal edge of the sheath does not hang up on tissue when it is advanced distally. The distal shroud 1630 is preferably fabricated from elastomeric materials such as, but not limited to, thermoplastic elastomer, silicone elastomer, polyurethane elastomer, and the like. The proximal end of the distal fairing 1630 affixed over the distal end of the balloon 1604 and may ride up over the tapered part of the balloon 1604. When the balloon 1604 expands, the distal fairing 1630 can expand therewith. When the balloon 1604 is re-collapsed, the distal fairing 1630 re-compresses and can be withdrawn proximally through the expanded sheath tubing (not shown).

FIG. 17A illustrates a radially expandable sheath system 1700, shown in its radially compressed configuration, comprising a dilator 1600 and an expandable trans-septal sheath 1400. The sheath 1400 further comprises a proximal anchor 1506, a distal anchor 1508, a sheath radiopaque marker 1702, a chevron transition zone 1704, a plurality of distal infusion ports or holes 1006, and a fold line 1714. The dilator 1600 further comprises a dilatation balloon 1604, an inner dilation tube 1610, and a penetrator 1302. The penetrator 1302 is shown extended beyond the distal end of the inner dilator tubing 1610. The dilator 1600 comprises the dilator hub 1320 (FIG. 13), which is affixed to the dilator shaft 1302. The dilator hub 1320, in an embodiment, further comprises anti-rotation elements (not shown) to prevent it from rotating relative to the sheath hub 1406 (FIG. 14). In an embodiment, such anti-rotation elements can include tabs on the dilator hub 1320 and slots on the sheath hub 1406, or visa versa, which can disengage by simple axial retraction of the dilator hub 1320 proximally away from the sheath hub 1406. The anti-rotation elements can prevent inadvertent distortion of the sheath system 1700 during insertion and manipulation inside the patient. The dilator 1600 can further comprise a fairing or distal shroud (not shown) that prevents the distal edge of the folded sheath tubing 1404 from catching on tissue as it is being advanced distally. This distal shroud serves as a shoehorn to ensure that the sheath 1400-dilator 1600 combination 1700 can be smoothly advanced through a tissue puncture or endovascular lumen without becoming caught or hung up. The distal shroud is preferably elastomeric to expand with the dilatation balloon 1604 and is affixed at its distal end to the dilatation balloon 1604 or inner dilator tubing 1610, or both. The distal shroud retracts distally away from the expandable distal section 1404 of the sheath 1400 because it is affixed to the dilator 1600. The infusion ports or holes 1006 are distorted and folded along with the distal end of the sheath 1400. The infusion holes or ports 1006 can be distal to, or proximal to, the distal anchor 1508.

FIG. 17B illustrates the sheath system 1700 in its radially or diametrically expanded configuration. The sheath system 1700 comprises the dilator 1600 and the sheath 1400. Also shown in FIG. 17B are the chevron transition zone 1704, the proximal balloon anchor 1506, the distal balloon anchor 1508, a plurality of drainage or infusion holes or ports 1006, the anchor inflation line 1332, the steering linkage lumen 1424, and the sheath radiopaque marker 1702. The dilatation balloon 1604 is shown in its expanded, inflated configuration over the inner dilator tubing 1610. When the dilator balloon 1604 is deflated, the distal shroud (not shown) collapses diametrically and can be easily pulled proximally through the expanded tubing 1404 as the dilator 1600 is being withdrawn. The infusion holes 1006 are shown expanded and non-distorted following expansion of the expanded tubing 1404. In this embodiment, the dilator 1600 comprises a hub 1320, which is affixed to a "T" or "Y" fitting 1720. The "T" or "Y" fitting 1720 is operably connected to the guidewire lumen of the dilator 1600. The "T" or "Y" fitting 1720 further comprises a stopcock 1724 or other valve affixed to the sideport and a Tuohy-Borst fitting 1722 affixed to and operably connected to the guidewire port. The "T" or "Y" fitting 1720 permits infusion of antithrombogenic liquid or fluid or radiopaque contrast media into the guidewire lumen thus minimizing the risk of thrombus forming or the generation of thromboemboli between the guidewire and the guidewire lumen walls within the dilator 1600. The stopcock 1724 allows the infusion port or sideport to be closed off, thus preventing fluid flow through the sideport.

FIG. 17C illustrates the sheath 1400 after removal of the dilator 1600 (FIGS. 17A and 17B). The sheath 1400 further comprises the sheath hub 1406, the lever 1420, the proximal tubing 1402, the distal tubing 1404, the proximal anchor 1506, the distal anchor 1508, a plurality of infusion or drainage holes or ports 1006, the sheath radiopaque marker 1702, and the transition zone 1704. The sheath 1400 is fully expanded at its distal end 1404 and the proximal and distal anchors 1506 and 1508 are deflated. The proximal tubing 1402, the distal tubing 1404, or both can be fabricated using composite construction comprising a lubricious inner layer, a reinforcing layer, and an outer lubricious layer. Suitable materials for use in fabricating the inner layer and the outer layer include, but are not limited to, polyurethane, polyethylene, polypropylene, Hytrel, PEBAX, polyamide, and the like. Wall thicknesses of these layers can range from 0.0005 to 0.025 inches and preferably between 0.001 and 0.010 inches. In another embodiment, an elastomeric layer can be disposed outside the reinforcing layer and under the outer layer. In yet another embodiment, an elastomeric layer can be disposed between the reinforcing layer and the inner lubricious layer. The elastomeric layer can be fabricated from materials such as, but not limited to, thermoplastic elastomer, silicone elastomer, polyurethane elastomer, C-Flex, or the like. The proximal tubing 1402 in another embodiment, can be configured with a plurality of lumens to control the motion of multiple catheters that can be inserted therethrough. In an exemplary embodiment, the proximal tubing 1402 comprises two lumens that can each accept an 8 French catheter, or smaller, inserted therethrough. The lumens can be discreet or the separator wall can be removed at least in part to minimize catheter size. In the multiple lumen embodiment of the proximal region, the dilator 1600 can be inserted through one of the lumens. The cross-sectional shape of the proximal tubing 1402 can further be configured as non-circular to minimize the cross-sectional area while two round catheters, such as EP ablation or diagnostic catheters, are inserted therethrough. The distal region 1404 can be similarly ovalized or non-round but, because of its malleable nature, the distal region 1404 can be made capable of simply deforming to accept the two or more catheters. The sheath hub 1406 can further be configured with dual hemostasis valves and further include "Y" guides to facilitate placement of dual (or more) catheters therethrough.

Figure 18A:
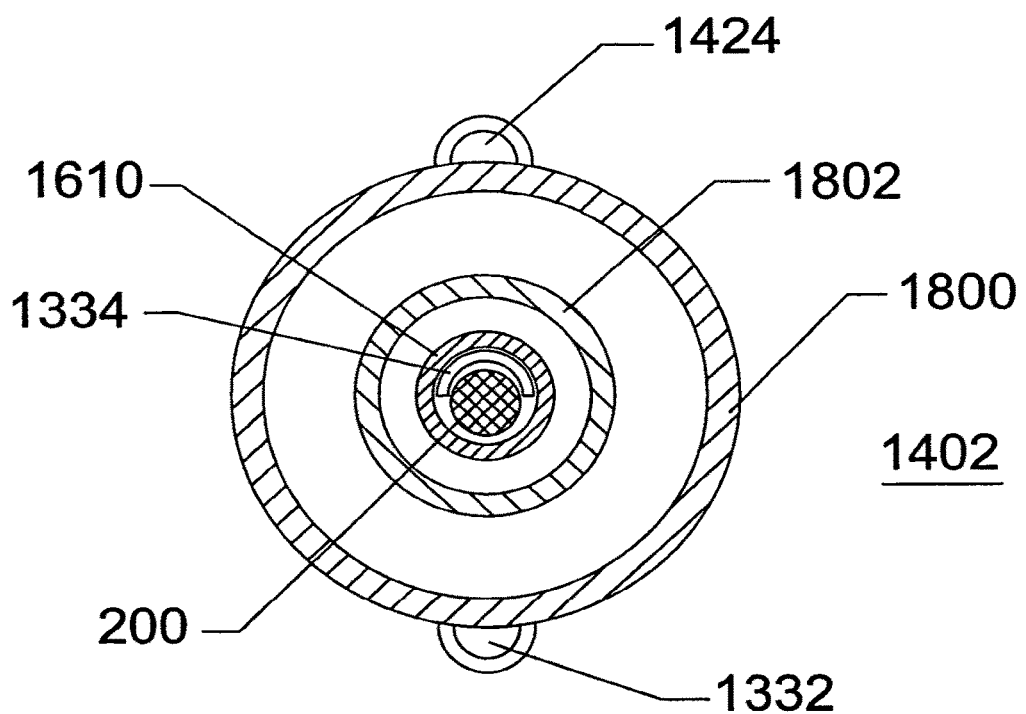
FIG. 18A illustrates a lateral cross-section of the proximal region of the expandable trans-septal sheath, according to an embodiment of the invention.

FIG. 18A illustrates a cross-sectional view of the sheath proximal end 1402. The proximal region 1402 further comprises the sheath tubing 1800, the outer dilator tubing 1802, the inner dilator tubing 1610, the guidewire 200, the penetrator linkage 1334, the steering linkage lumen 1424, and the anchor inflation lumen 1332. The sheath tubing 1800 is, in an embodiment, a composite tube with an inner layer of lubricious material, an outer layer, and an intermediate reinforcing layer fabricated from a coil or braid. The coil or braid in the proximal region 1402 possesses spring characteristics and is fabricated from stainless steel, titanium, nitinol, cobalt-nickel alloys, or the like. The coil or braid can also be fabricated from polymers such as PET, PEN, polyamide, HDPE, or the like. In an exemplary embodiment, the reinforcing layer is a braid of PEN. The coil configuration can be fabricated from flat wire or from round wire. The coil or braid can be coated with radiopaque materials such as gold, tantalum, platinum, or the like, to enhance radiopacity. More than one steering linkage lumen 1424 can be used to achieve push-pull action, if separated by 180 degrees, or two axis steering if separated by 90 degrees, or 120 degrees, for example.

Figure 18B:
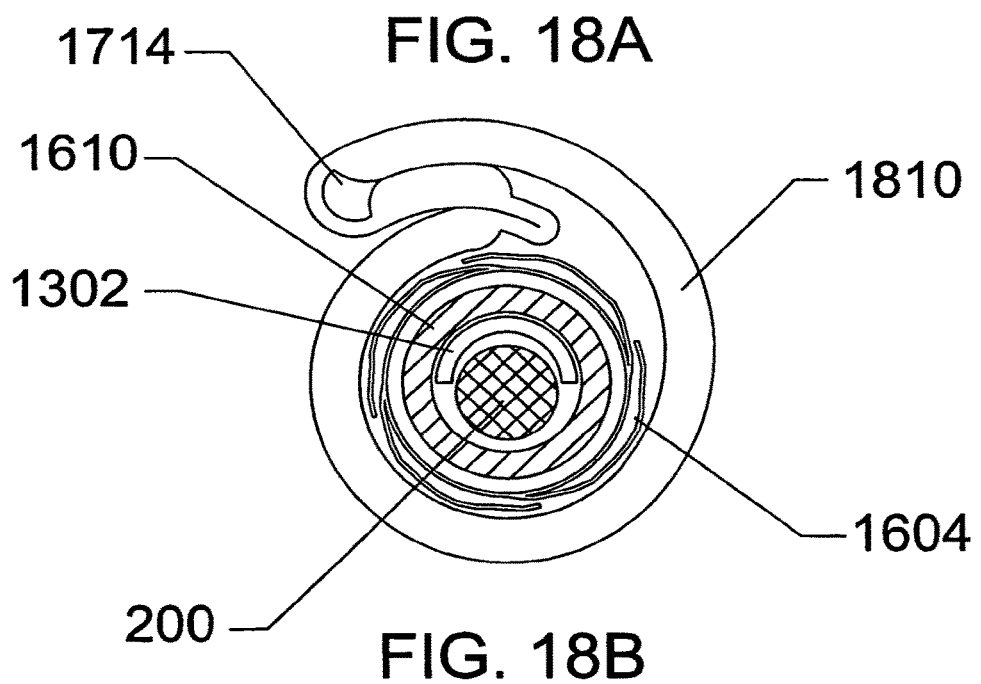
FIG. 18B illustrates a lateral cross-section of the distal region of the expandable trans-septal sheath in its non-expanded configuration, according to an embodiment of the invention.

FIG. 18B illustrates a cross-sectional view of the sheath distal region 1404 in its collapsed configuration. The sheath 1404 further comprises the distal expandable tubing 1810, the collapsed dilatation balloon 1604, the anchor inflation lumen 1332, the guidewire 200, the penetrator 1302, the inner dilator tube 1610, one or more longitudinal folds 1714, and the steering linkage lumen 1424. The distal expandable tubing 1810 is, in an embodiment, a composite structure with an inner layer, an outer layer, both of which are formed from polymers similar to those used in the proximal region 1402, and an intermediate malleable reinforcing layer, preferably fabricated from annealed metals such as, stainless steel, gold, platinum, tantalum, or the like. In an exemplary embodiment, the malleable reinforcement comprises a coil of stainless steel 304, which has been substantially annealed. The stainless steel is formed into a flat wire with a thickness of 0.002 to 0.004 inches and a width of 0.010 to 0.040 inches. The flat wire is formed into a coil with a spacing substantially the same as the width of the flat wire. The stainless steel wire can be coated with a layer of gold to a thickness of 100 angstroms or more. Enhanced radiopacity can be gained by winding coils of gold wire alongside the stainless steel wire. The configuration, in this embodiment is of a double helical spring where the helical elements run parallel to each other. Typical gold wire suitable for such use has a diameter of 0.001 inches to 0.009 inches. The gold wire can be round or it can be flat wire. It is important that the gold wire not fill the entire space between the stainless steel wires so that some polymer can fill the space between substantially most of the coils.

Figure 19:
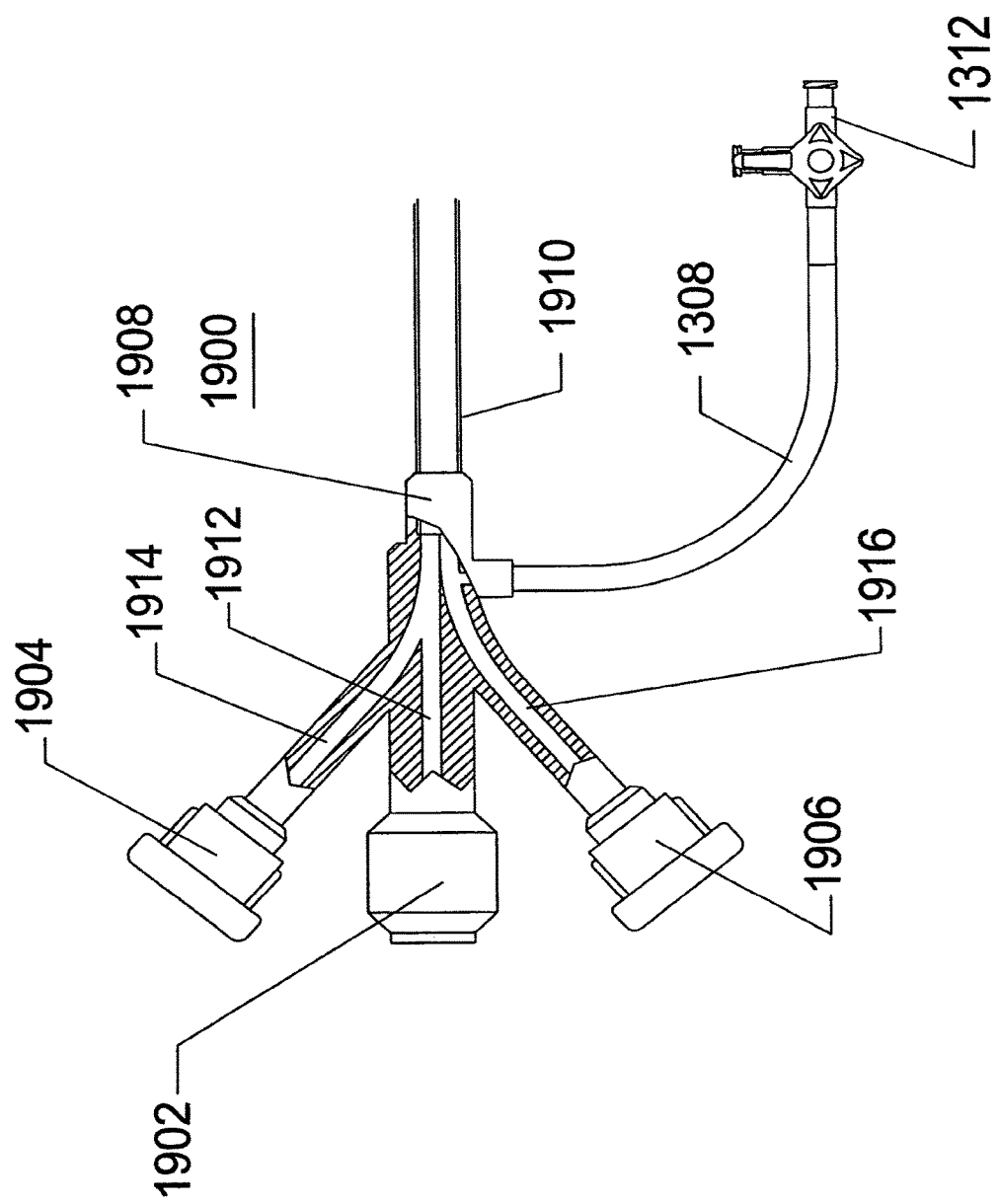
FIG. 19 illustrates a partial breakaway side view of a proximal end of a trans-septal sheath comprising multiple instrumentation ports on its hub, according to an embodiment of the invention.

FIG. 19 illustrates a side view of a proximal end of a trans-septal sheath 1900 comprising multiple instrumentation ports 1902, 1904, and 1906 on its hub 1908, a length of proximal sheath tubing 1910, a straight through hub lumen 1912, an upper hub lumen 1914, a lower hub lumen 1916, a fluid infusion line 1308, and a fluid infusion line stopcock 1312. The hub 1908 is shown in partial breakaway view to better illustrate interior details. The trans septal sheath 1900 is capable of accepting two or more catheters simultaneously therethrough. One catheter is typically routed through the upper instrumentation port 1904, the upper hub lumen 1914 and finally into the lumen of the proximal sheath tubing 1910. Another catheter can be routed, at the same time, through the lower instrumentation port 1906, the lower hub lumen 1916 and into the lumen of the proximal sheath tubing 1910. The straight through hub port 1902 and the straight through hub lumen 1912 are used for insertion of guidewires and for insertion of a dilator such as the one shown in FIG. 16. The straight through hub lumen 1912 can align with the center of the through lumen of the sheath tubing 1910 or it can be offset to correspond to the center of a separate lumen or cross-sectional orifice. The ports 1902, 1904, and 1906 are preferably hemostatic valves such as a Tuohy-Borst device, ball valve, duckbill valve, or similar.

Figure 20:
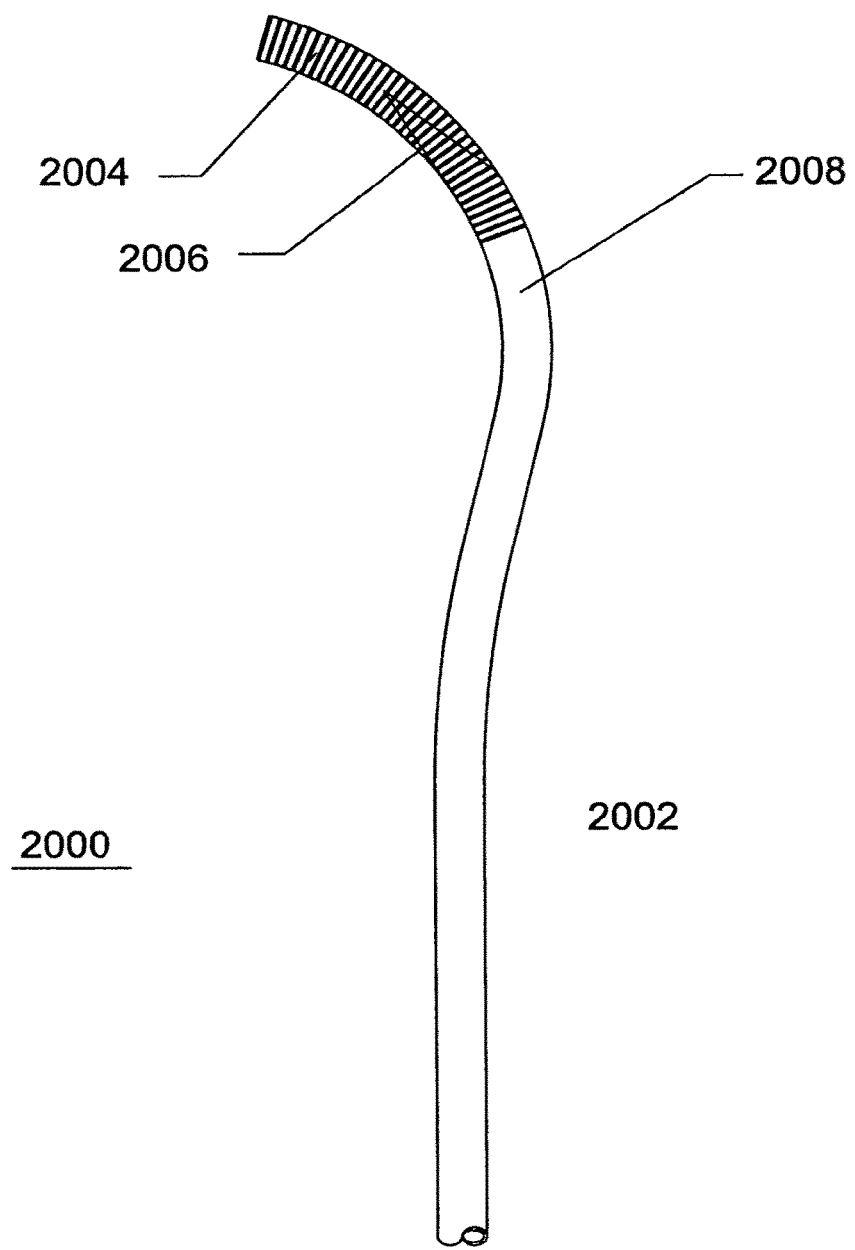
FIG. 20 illustrates a side view of a distal end of a trans-septal sheath and dilator comprising curvature near its distal end to facilitate trans-septal puncture, according to an embodiment of the invention.

FIG. 20 illustrates a side view of a distal end of a trans-septal sheath 2000 comprising curvature 2008 near its distal end to facilitate trans-septal puncture. The sheath 2000 further comprises a non-expandable region 2002, an expandable region 2004, and a transition zone 2006 that separates the expandable region 2004 from the non-expandable region 2002. The curvature is imparted in a first plane in the illustrated embodiment. The curvature 2008 is imparted onto the non-expandable region 2002 but may also be imparted onto at least a portion of the expandable region 2004. In an exemplary embodiment, the curvature 2008 is imparted onto both a portion of the distal end of the non-expandable region 2002, the entire transition zone 2006, and a proximal portion of the expandable region 2004. The radius of curvature is approximately 7.5 cm and a proximal portion of the curved zone 2008 is curved outward away from the direction in which the distal end of the sheath 2000 points. In another embodiment, there can also be curvature 2008 out of the first plane into a second plane. The curvature can be such that a right-handed or left-handed twist or spiral configuration results. The retrograde curvature is advantageous in stabilizing the distal end of the sheath 2000 within the cardiovascular system while other instrumentation are being passed therethrough.

FIG. 21A illustrates an embodiment of a lateral cross-sectional profile of a proximal end of a sheath comprising a non-circular outer profile and a dual partial lumen inner profile. In this embodiment, the proximal tubing 2100 is suitable for conveying a catheter through each of its two lumens 2102. Said catheter passage may be simultaneous, sequential, or one at a time. The proximal tubing 2100 comprises a separation wall 2104, a plurality of side walls 2108, and rounded end walls 2106. The cross-section of a round sheath 2110 is illustrated with dashed lines to show the additional area required to maintain the same two catheter lumens. In this embodiment, a sheath with the rounded cross-section would exceed 18 French to carry two 8-French catheters and have 0.013-inch thick walls while the oval embodiment would approximate 15.5 French to 16 French for the same carrying capacity. The reduced cross-sectional area is beneficial to reduce the size of the wound necessary for arterial or venous access and could make the difference between a cutdown and a percutaneous procedure. In another embodiment, the separation wall 2104 could be eliminated to further reduce cross-sectional size. In yet another embodiment, the separation wall 2104 can only partially protrude inward from the side walls 2108 and thus serve as a catheter guide without completely separating the lumens. Such configurations are beneficial in preventing two catheters from twisting or interfering with each other while both are being placed. The partially or completely separated lumens 2102 can extend partially or completely along the proximal non-expandable region of the sheath. In yet another embodiment, the interior of the sheath 2100 is oval and approximately matches the exterior geometry of the sheath.

FIG. 21B illustrates an embodiment of a lateral cross-sectional profile of a distal, expandable region 2150 of a sheath in the region of curvature 2008 (refer to FIG. 20). The distal expandable region 2150, shown in the collapsed state, comprises a malleable reinforced wall 2152, a plurality of folded regions 2154, and a plurality of fold edges 2156. The dilator is shown inserted through the distal region 2150 and the inner tube 1610 and the folded balloon 1604 are illustrated. The fold edges 2156 are preferably oriented along the inside of the curve 2008. If the fold edges 2156 are oriented differently, the structure has a greater chance of buckling or kinking. If a single fold 2154, rather than two folds 2154 are used, the single fold 2154 is oriented in the direction of the inside of the curvature 2008.

The present invention may be embodied in other specific forms without departing from its spirit or essential characteristics. For example, the sheath may include instruments affixed integrally to the interior central lumen of the sheath, rather than being separately inserted, for performing therapeutic or diagnostic functions. The hub may comprise tie downs or configuration changes to permit attaching the hub to the mouth, nose, or face of the patient. The dilatation means may be a balloon dilator as described in detail herein, it may rely on axial compression of a braid to expand its diameter, or it may be a translation dilator wherein an inner tube is advanced longitudinally to expand an elastomeric small diameter tube. Dilation may also occur as a result of unfurling a thin-film wrapped tube or by rotation of a series of hoops so that their alignment is at right angles to the long axis of the sheath. The embodiments described herein further are suitable for fabricating very small diameter catheters, microcatheters, or sheaths suitable for cardiovascular or neurovascular access. Various valve configurations and radiopaque marker configurations are appropriate for use in this device. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of instrumenting a left atrium of a patient comprising the steps of:
   routing a guidewire into the right atrium from a peripheral vein;
   inserting a sheath with a distal region in a collapsed state and a pre-inserted dilator into the patient over the guidewire; the collapsed state of the distal region having a plurality of folded regions forming two outer fold edges that are oriented adjacent to each other, and forming two inner fold edges that are oriented apart and across from each other;
   advancing the sheath to a treatment or diagnostic site within the right atrium of the heart;
   performing a trans-septal puncture between the right and left atrium and advancing the distal region in the collapsed state through the puncture into the left atrium;
   dilating with a dilation balloon of the pre-inserted dilator the distal region of the sheath to an expanded state so that the distal region of the sheath is expanded to dilate the puncture and increase a diameter of a distal end of a lumen extending through the sheath;
   maintaining a position of the distal region of the sheath into the left atrium by inflating a distal balloon of the sheath in the left atrium and inflating a proximal balloon of the sheath in the right atrium, so as to engage the atrial septum,
   collapsing the dilator; removing the dilator from the sheath; inserting instrumentation through the lumen of the sheath into the left atrium; said instrumentation being larger in diameter than said distal end of said lumen when said distal region of said sheath is in a collapsed state; performing therapy or diagnosis with the instrumentation; and
   removing the sheath from the patient.

2. The method of claim 1 wherein dilating the distal region comprises inflating a balloon on the dilator.

3. The method of claim 1 wherein dilating the distal region comprises attaching a liquid-filled inflation device to a balloon inflation port at the distal end of the dilator and infusing liquid under pressure into the dilator.

4. The method of claim 3 wherein collapsing the dilator comprises withdrawing a plunger on the inflation device to withdraw liquid from the dilator.

5. The method of claim 1 wherein performing therapy or diagnosis with the instrumentation comprises electrophysiology energy delivery.

6. The method of claim 1 wherein inserting instrumentation through the lumen of the sheath comprises inserting two or more catheters through the sheath to perform the therapy.

7. The method of claim 1 wherein performing therapy or diagnosis with the instrumentation comprises delivering an implant into the left atrium.

8. The method of claim 1 wherein dilating the distal region also comprises dilating anchors within the atria.

9. The method of claim 1 wherein the lumen created in the distal region by the dilator is substantially larger than the lumen in a proximal region of the sheath.

10. The method of claim 1, wherein the distal balloon and the proximal balloon both anchor said sheath relative to said atrial septum.

11. The method of claim 1, wherein the distal balloon and the proximal balloon are both configured to inflate through a single, first inflation lumen.

12. A method of instrumenting a left atrium of a patient comprising the steps of:
   routing a guidewire into the right atrium from a peripheral vein;
   inserting a sheath with a distal region in a collapsed state and a pre-inserted dilator into the patient over the guidewire; the collapsed state of the distal region having a plurality of folded regions forming two outer fold edges that are oriented adjacent to each other, and forming two inner fold edges that are oriented apart and across from each other;
   advancing the sheath to a treatment or diagnostic site within the right atrium of the heart;
   performing a trans-septal puncture between the right and left atrium and advancing the distal region in the collapsed state through the puncture into the left atrium;
   dilating with a dilation balloon of the pre-inserted dilator the distal region of the sheath to an expanded state so that the distal region of the sheath is expanded to dilate the puncture and increase a diameter of a distal end of a lumen extending through the sheath;
   maintaining a position of the distal region of the sheath into the left atrium by inflating a dumbbell shaped balloon of the sheath, wherein a distal balloon portion of the dumbbell shaped balloon expands in the left atrium, a proximal balloon portion of the dumbbell shaped balloon expands in the right atrium and a middle portion of the dumbbell shaped balloon resides within the trans-septal puncture,
   collapsing the dilator; removing the dilator from the sheath; inserting instrumentation through the lumen of the sheath into the left atrium; said instrumentation being larger in diameter than said distal end of said lumen when said distal region of said sheath is in a collapsed state; performing therapy or diagnosis with the instrumentation; and
   removing the sheath from the patient.

* * * * *